(12) United States Patent
Gullberg et al.

(10) Patent No.: US 10,669,569 B2
(45) Date of Patent: Jun. 2, 2020

(54) DYNAMIC RANGE METHODS

(75) Inventors: Mats Gullberg, Sollentuna (SE); Irene Weibrecht, Heidelberg (DE); Carl-Magnus Clausson, Uppsala (SE); Ola Söderberg, Österbybruk (SE)

(73) Assignee: Navinci Diagnostics AB, Uppsala (SE)

( * ) Notice: Subject to any disclaimer, the term of this patent is extended or adjusted under 35 U.S.C. 154(b) by 48 days.

(21) Appl. No.: 13/879,038

(22) PCT Filed: Oct. 14, 2011

(86) PCT No.: PCT/EP2011/068039
§ 371 (c)(1),
(2), (4) Date: Jul. 9, 2013

(87) PCT Pub. No.: WO2012/049316
PCT Pub. Date: Apr. 19, 2012

(65) Prior Publication Data
US 2013/0288249 A1    Oct. 31, 2013

(30) Foreign Application Priority Data

Oct. 15, 2010  (GB) .................................. 1017440.7
May 24, 2011  (GB) .................................. 1108637.8

(51) Int. Cl.
*C12Q 1/68* (2018.01)
*C12Q 1/6804* (2018.01)
*G01N 33/542* (2006.01)

(52) U.S. Cl.
CPC ............ *C12Q 1/68* (2013.01); *C12Q 1/6804* (2013.01); *G01N 33/542* (2013.01)

(58) Field of Classification Search
USPC ............ 435/6.1, 6.11, 6.12, 91.1, 91.2, 183; 436/94, 501; 536/23.1, 24.3, 24.33, 25.3
See application file for complete search history.

(56) References Cited

U.S. PATENT DOCUMENTS

| 4,514,505 A | 4/1985 | Canfield et al. |
| 5,585,241 A | 12/1996 | Lindmo |

(Continued)

FOREIGN PATENT DOCUMENTS

| WO | 97/00446 A1 | 1/1997 |
| WO | 99/23490 A1 | 5/1999 |

(Continued)

OTHER PUBLICATIONS

Ericsson et al, Nucleic Acids Research, 36(8):c45,1-9 (Feb. 29, 2008).

(Continued)

*Primary Examiner* — Frank W Lu
(74) *Attorney, Agent, or Firm* — Porter Wright Morris & Arthur LLP

(57) ABSTRACT

Methods for detecting and quantifying an analyte employ a pair of proximity probes, each comprising a proteinaceous target-binding domain coupled to a nucleic acid domain (NAD), which NADs interact when the proximity probes have bound in proximity to their respective target; and a set of markers, wherein each marker is a nucleic acid molecule comprising a binding domain and a reporter domain giving a detectable signal, can interact with said NADs to form a nucleic acid molecule from which a detectable signal is generated, or with a nucleic acid molecule generated by interaction of said NADs, cannot interact with said NADs simultaneously with another marker in the set, generates a signal that is distinguishable from another marker signal, and is present in an amount capable of detecting analyte at a range of concentrations differing from the range of concentrations detectable by other markers.

18 Claims, 7 Drawing Sheets

Specification includes a Sequence Listing.

(56) References Cited

U.S. PATENT DOCUMENTS

| | | | |
|---|---|---|---|
| 5,665,539 | A | 9/1997 | Sano et al. |
| 6,511,809 | B2 | 1/2003 | Baez et al. |
| 6,551,788 | B1 | 4/2003 | Bell |
| 6,558,928 | B1 | 5/2003 | Landegren |
| 7,306,904 | B2 | 12/2007 | Landegren |
| 7,320,860 | B2 | 1/2008 | Landegren |
| 2003/0105320 | A1 | 6/2003 | Becker et al. |
| 2003/0235849 | A1 | 12/2003 | Lizardi et al. |
| 2004/0248103 | A1 | 12/2004 | Feaver et al. |
| 2006/0246475 | A1 | 11/2006 | Peterson et al. |
| 2007/0026430 | A1 | 2/2007 | Anderson et al. |
| 2008/0274458 | A1 | 11/2008 | Latham et al. |
| 2010/0311185 | A1 | 12/2010 | Schlep et al. |

FOREIGN PATENT DOCUMENTS

| | | | |
|---|---|---|---|
| WO | 01/61037 | A1 | 8/2001 |
| WO | 01/79844 | A2 | 10/2001 |
| WO | 03/012119 | A2 | 2/2003 |
| WO | 03/044231 | A1 | 5/2003 |
| WO | 2005/123963 | A2 | 12/2005 |
| WO | 2007/044903 | A2 | 4/2007 |
| WO | 2007/053594 | A2 | 5/2007 |
| WO | 2007/107743 | A1 | 9/2007 |
| WO | 2009/012220 | A2 | 1/2009 |

OTHER PUBLICATIONS

Weibrecht et al, Expert Reviews Proteomics, 7(3):401-409 (Jun. 1, 2010).

Soderberg et al, Methods, 45(3):227-232 (Jul. 1, 2008).

Landegren et al, A Ligase-Mediated Gene Detection Technique, Science, vol. 241, pp. 1077-1080, Aug. 26, 1988.

Larsson et al, In situ genotyping individual DNA molecules by target-primed rolling-circle amplification of padlock probes, Nature Methods, vol. 1, No. 3, pp. 227-232, Dec. 2004.

Larsson et al, In situ detection and genotyping of individual mRNA molecules, Nature Methods, vol. 7, No. 5, pp. 395-397 and online supplement, published online Apr. 11, 2010.

Pohl et al, Principle and applications of digital PCR, Expert Rev. Mol. Diagn. 4(1), pp. 41-47, (2004).

Schweitzer et al, Immunoassays with rolling circle DNA amplification: A versatile platform for ultrasensitive antigen detection, PNAS, Aug. 29, 2000, vol. 97, No. 18, pp. 10113-10119.

Soderberg et al, Direct observation of individual endogenous protein complexes in situ by proximity ligation, Nature Methods, published online Oct. 29, 2006.

Stromberg et al, Multiplex Detection of DNA Sequences Using the Volume-Amplified Magnetic Nanobead Detection Assay, Analytical Chemistry, vol. 81, No. 9, pp. 3398-3406, May 1, 2009.

Di Guisto et al, Proximity extension of circular DNA aptamers with real-time protein detection, Nucleic Acids Research, vol. 33, No. 6, e64, published online Apr. 7, 2005.

Fredriksson et al, Protein detection using proximity-dependent DNA ligation assays, Nature Biotechnology, vol. 20, pp. 473-477 (2002).

Gullberg et al, Cytokine detection by antibody-based proximity ligation, PNAS, vol. 101, No. 22, pp. 8420-8424 (2004).

Jarvius et al, Digital quantification using amplified single-molecule detection, Nature Methods, vol. 3, No. 9, pp. 725-727, Sep. 2006.

DYNAMIC RANGE METHODS

The Sequence Listing submitted herewith, entitled "March-9-2020-Sequence-Listing-ST25.txt", created Mar. 9, 2020 and having a size of 2957 bytes, is incorporated herein by reference.

The present invention relates to methods for detecting and quantifying an analyte in a sample, principally in proximity probe assays, and in particular to an improvement in such methods to extend the dynamic range of detection, which is particularly advantageous for the detection and quantification of an analyte where the concentration range of the analyte in said sample is unknown and/or the range is likely to be broad. The improvement comprises the provision of a set of markers with a defined composition for use in such methods, particularly in proximity probe based methods. The composition is designed to comprise at least two substantially similar markers (reporter molecules), which each generates a distinct signal on interaction with the analyte (directly or indirectly, e.g. via interaction with a set of proximity probes, e.g. a proximity probe pair) and wherein each marker is present in a predefined ratio, i.e. in an amount capable of detecting the analyte in a concentration range that differs from the range of analyte concentrations detectable by other markers in the sample. The composition is added to the sample such that at least one of the markers will generate a signal that is above the lowest limit of detection and below the point of saturation. Thus, in the present invention the observable effect of the marker composition is to increase the dynamic range of the assay, thereby improving the accuracy and sensitivity of the methods for detecting and quantifying an analyte. The present invention also provides marker composition and a kit comprising said composition.

A wide variety of assays exist for the detection and quantification of an analyte in a sample and a common feature of such assays is the use of a marker (reporter molecule) to indicate the presence of said analyte. Generally, such markers interact with the analyte (directly or indirectly), wherein said interaction results in the generation of a signal (directly or indirectly), which can be detected (directly or indirectly) and used determine, quantitatively or qualitatively, the amount or existence of said analyte in the sample. However, to obtain quantitative measurements it is of outmost importance to measure non-saturated signals. In fact, saturation of signals is a common reason for limited dynamic range in many quantitative assays, including quantitative imaging. A limiting factor in such assays is often the dynamic range of the marker and this is compounded when the likely concentration range of the analyte of interest is unknown.

The dynamic range (DR or DNR) is the ratio between the smallest and largest possible values of a changeable (i.e. variable) quantity. The dynamic range of an analyte in a sample will depend on the nature of the sample, e.g. source and size, and the analyte, e.g. a DNA molecule may be present as a single copy in a cell, whereas there may be hundreds or thousands of copies of the protein encoded by said DNA molecule in the same cell and still further there may be, for example, tens or hundreds of thousands of metabolites produced by said proteins. Thus, a single type of analyte in a typical biological sample could encompass a dynamic range from a single molecule to a molar concentration, e.g. the receptor HER2 (Erbb2) can be present a quantities of up to 2,000,000 receptors per cell whereas a neighbouring cell can have as few as 10 receptors (or of course none at all), and to be able to detect and quantify an analyte in a sample where the analyte could be present in such a range of concentrations would require a marker with a DR of at least 1:200,000, i.e. a marker capable producing a detectable signal for a single molecule, whilst also capable of producing a non-saturated signal in the presence of 2,000,000 molecules. A marker with a dynamic range of less than 1,000 would not be useful for analysing different samples where the concentration of the analyte could range, e.g. from pM to nM, or nM or μM, or μM or mM etc.

In a situation where the expected concentration range of an analyte is unknown or the potential concentration range of the sample is broad, one option is to generate a serial dilution of the sample and/or the marker and perform a variety of assays combining the various dilutions to determine the optimum conditions at which the analyte can be detected in the sample. This is can result in a large number of assays to be performed for a single analyte. Where the sample comprises more than one analyte of interest, the number of assays required can quickly escalate, particularly where the markers for each analyte have different detection limits, e.g. if the markers are antibodies with divergent binding affinities for their corresponding analytes. This may also preclude detecting the different analytes in a single assay and may make it impossible to detect an analyte in a rare or small sample, i.e. where there is an insufficient amount of the sample to perform multiple assays.

The limits of the dynamic range in a quantitative analysis are applicable to a large number of diverse fields. For example, microscopy images of cells and tissues stained with labelled reagents are frequently used as a means to evaluate and quantify the presence of a specific target antigen within a sample. There exist several ways to estimate the relative amount of target within a sample but there may be a severe limit on the extent of the dynamic range. In some applications the actual number of pixels in the imaging unit used for capturing images could be the limiting factor, e.g. the resolution in a standard microscopy is limited by the wavelength of light and a single source of light, which is not smaller than 400 nm. In a cell with a diameter of just 10 μm there would be no more than 625 different points of light-sources that could be detected. Hence, when using intensity as a measurement in microscopy, the dynamic range may be limited by several factors including background noise and signal, but also the quality of the camera. For instance, the range is often not more than a factor of 100 between limit of detection and saturating levels and very rarely more than 1000.

As a comparison, the limit on dynamic range for digital-PCR is set by the number of wells used per sample. The sample is diluted to ensure only a subset of all wells contain a target molecule. Thus, when the concentration of the analyte in the sample is unknown the vast majority of wells will be empty, especially for samples that contain low amounts of the target analyte. This severely limits the utility of the method, decreases through-put and increases costs as a large number of reactions are required to obtain an accurate measurement of target analyte.

As mentioned above, several factors can be seen to play a part in limiting the dynamic range of an assay. For example, background "noise" will affect the limits of detection and it will be understood that the dynamic range cannot extend below the background level of signal contributed by the detection of, e.g. a non-specific label. Thus, as the background noise increases, so the dynamic range decreases. A further factor in the limits of the dynamic range is the maximum amount of signal that is capable of being detected. Hence, if an instrument is only capable of detecting accurately a signal of 1,000, then any signal above this threshold will not be registered and the dynamic range of the assay will be limited by this value.

Various techniques to overcome these limitations have been sought and these tend to focus on decreasing the signal:noise ratio. This can be achieved, e.g. by lowering the background noise or increasing the maximum signal that can be detected. Techniques to lower background are well known in the art, e.g. increasing sample number to reduce the experimental error, using serial dilutions or blocking reagents to decrease or neutralise contaminants that result in background signal, increasing the specificity of the assay etc. Other approaches have relied on improving the detection apparatus used or in mathematical algorithms for analysing the data.

However, it is evident that further methods to increase, improve or extend the dynamic range of quantitative assays are required, i.e. to obtain non-saturated signals in an assay, and the present invention addresses this need.

The novel approach provided by the present invention is to provide a reporter molecule (namely a molecule which may "report" (or indicate) the presence of an analyte, e.g. a molecule capable of interacting, directly or indirectly, with the analyte to be detected) with two or more different labels in a predefined ratio to create a reporter molecule composition. The result of this dual/multiple labelling is such that a single reporter molecule composition can be used to detect a broad concentration range of analyte. As such there is no need to produce dilutions of the sample or to alter the parameters of the assay as described above.

In its simplest form the method of the invention can be described using the following example, where reporter molecule A may be used to detect analyte B. A reporter molecule composition is created where 20% of reporter molecule A is labelled with label X and 80% of reporter molecule A is labelled with label Y. This reporter molecule composition is equally useful in determining the amount of analyte B in two samples, where sample 1 contains low levels of analyte B and sample 2 contains high levels of analyte B.

In sample 1, where analyte B is present at a low concentration, there will be a low level of signal from label X (e.g. below the minimum level of detection or below the level of background noise), but sufficient signal from label Y to provide an accurate quantification of the analyte (see FIG. 1A).

In sample 2, where analyte B is at high levels, the signal from label Y will be very high (e.g. above the level of saturation), but the signal from label X should be below levels of saturation and thus capable of providing an accurate quantification of the analyte (see FIG. 1B).

In a sample with intermediate levels of analyte, both labels may produce a signal that is below the saturation level and above the limit of detection, thereby providing two independent measurement values and a more accurate measure of the analyte level (see FIG. 1C).

Thus, the method of the present invention may be used in combination with other methods to further increase the dynamic range of the assay, e.g. use of blocking reagents. Furthermore, it is evident that by using multiple labelled reporter molecules in a predefined ratio in a single assay, e.g. 1:5:25 of reporter molecule A labelled with X:Y:Z, it is possible to further extend the dynamic range of the assay.

It will be apparent from above hypothetical example and the discussion herein that the improvement provided by the present invention, namely a means of extending the dynamic range of an assay, is applicable to a diverse range of assays (e.g. any method that relies on labels to obtain quantitative data and particularly in object counting methods), such as, but not limited to, single molecule imaging; proximity assays, e.g. proximity ligation assays; immunoassays, e.g. ELISA, immuno-PCR, e.g. immuno-rolling circle amplification; gene-detection using rolling circle amplification, e.g. padlock probes; applications such as gene-copy measurements using FISH (fluorescent in situ hybridisation); or digital read-out formats such as digital-PCR. The methods described herein also have great advantages in methods that measure total intensities such as standard immunofluorescence and energy transfer assays, e.g. but not limited to FRET (fluorescence resonance energy transfer), BRET (bioluminescence resonance energy transfer), BiFC (Bimolecular fluorescence complementation).

Furthermore, it is evident that the method described herein differs significantly from the previously described methods for extending the dynamic range and these differences result in numerous advantages. The present invention is predicated on the surprising discovery that the use of differently labelled reporter molecules that compete for a single binding site of an analyte can be used to extend the dynamic range of an assay. This is contrary to teachings in the art which suggest that reporter molecules that compete for a single binding site would have the effect of averaging out the detectable signal obtained from the reporter molecules and would therefore not be useful in improving the dynamic range.

Hence, the method disclosed herein can be used, for example, to detect analytes that are too small to have multiple target binding domains. Furthermore, as the present invention requires the reporter molecule to have only a single binding affinity, that is to say that only a single type of reporter molecule is required for each analyte, it is not necessary to identify multiple reporter molecules that have identical or similar binding affinities for their respective target site (e.g. on the analyte). In methods where reporter molecules bind to more than one target site on the analyte, if each reporter molecule has a different binding affinity this will need to be taken into account in the final analysis of the signals that are generated, i.e. reporter molecules with a particularly high target binding affinity may bias the final signal. In contrast, if a single probe is used to bind to a single target site of the analyte, then this effect does not require consideration when calculating the amount of analyte.

Thus, the methods of the invention represent a significant advance over other methods of extending the dynamic range of assays known in the art. For example the methods described herein enable assays to have improved accuracy, e.g. by allowing several measurements to be taken from a single assay and are particularly useful for the detection and/or quantification of an analyte in a sample where concentration range of analyte is unknown. By extending the dynamic range of an assay it is possible to detect and/or quantify analytes in single sample, wherein said analytes are present at vastly different concentrations in the same sample.

In a particularly preferred aspect of the invention the methods of the invention are, and the markers are (or marker composition or set is) for use in, a proximity-probe based assay and the markers are nucleic acid molecules, e.g. oligonucleotides, that interact (directly or indirectly) with the proximity probes, particularly the nucleic acid domains of the proximity probes. The proximity probe-based detection assay (proximity assay) may be any of the assays known in the art, for example as described below, which use proximity probes to detect an analyte in a sample. Advantageously, the invention may be used in the context of assays in which at least two (or all) the proximity probes in the assay are based on protein-nucleic acid conjugates (i.e. comprise a proteinaceous analyte-binding domain coupled to a nucleic acid domain). Notably, such an assay will be a proximity ligation assay or a proximity extension assay, although the invention is not limited to detecting interactions between the nucleic acid domains of proximity probes based on ligation or extension (for example the interaction between the nucleic acid domains may be based on hybridisation, e.g. wherein the markers hybridise to the nucleic acid domains of at least one and preferably two or more proximity probes to generate a signal, wherein hybridisation is possible only when the probes are bound to the target analyte (or a binding partner thereof) in proximity).

Thus, a preferred aspect of the invention provides a method of detecting an analyte in a sample, said method comprising:

(i) contacting said sample with at least a pair of proximity probes each comprising a proteinaceous target-binding domain coupled to a nucleic acid domain (in particular such that said nucleic acid domains may be allowed to interact directly or indirectly when the proximity probes have bound in proximity to their respective target), said target being either the analyte or a binding partner for the analyte;

(ii) further contacting said sample with at least one set of markers which function to extend the dynamic range of detection of the method, wherein said set comprises at least two markers, wherein each marker is a nucleic acid molecule comprising a binding domain and a reporter domain which gives rise to a detectable signal, and each marker:

(a) is capable of interacting either with said nucleic acid domains (in particular when said probes have bound in proximity to their respective target) to form a nucleic acid molecule from which a detectable signal is generated, or with a nucleic acid molecule generated by interaction of said domains;

(b) cannot interact with said nucleic acid domains simultaneously with another marker in the set;

(c) generates a signal that is distinguishable from the signal of another marker in the set; and (d) is present in an amount capable of detecting the analyte at a range of concentrations that differs from the range of concentrations detectable by other markers;

(ii) allowing said markers to interact with said nucleic acid domains or said generated nucleic acid molecule; and (iii) detecting said signal.

At its broadest, the present invention can be seen to provide a method of detecting an analyte in a sample, which method comprises the use of a set of markers, comprising at least two markers, wherein each marker:

(a) is capable of interacting with said analyte and generating a detectable signal;

(b) cannot interact with the analyte simultaneously with another marker of the set;

(c) generates a signal that is distinguishable from the signal of another marker in the set; and (d) is present in an amount capable of detecting said analyte at a range of concentrations that differs from the range of analyte concentrations detectable by other markers.

Alternatively viewed, the invention can be seen as a method of obtaining a non-saturated signal in an assay for detecting an analyte in a sample, which method comprises the use of a set of markers, comprising at least two markers, wherein each marker:

(a) is capable of interacting with said analyte and generating a detectable signal;

(b) cannot interact with the analyte simultaneously with another marker in the set;

(c) generates a signal that is distinguishable from the signal of another marker in the set; and (d) is present in an amount capable of detecting said analyte at a range of concentrations that differs from the range of analyte concentrations detectable by other markers.

Viewed from yet another aspect, the invention can be seen as the use of a set of markers, comprising at least two markers, wherein each marker:

(a) is capable of interacting with said analyte and generating a detectable signal;

(b) cannot interact with the analyte simultaneously with another marker in the set;

(c) generates a signal that is distinguishable from the signal of another marker in the set; and (d) is present in an amount capable of detecting said analyte at a range of concentrations that differs from the range of analyte concentrations detectable by other markers, to detect an analyte in a sample.

In yet a further aspect, the invention can be seen as the use of a set of markers, comprising at least two markers, wherein each marker:

(a) is capable of interacting with said analyte and generating a detectable signal;

(b) cannot interact with the analyte simultaneously with another marker in the set;

(c) generates a signal that is distinguishable from the signal of another marker in the set; and (d) is present in an amount capable of detecting said analyte at a range of concentrations that differs from the range of analyte concentrations detectable by other markers, to obtain a non-saturated signal in an assay for detecting an analyte in a sample.

The invention can also be seen to provide a composition for use in the methods of the invention comprising a set of markers, comprising at least two markers, wherein each marker:

(a) is capable of interacting with said analyte and generating a detectable signal;

(b) cannot interact with the analyte simultaneously with another marker in the set;

(c) generates a signal that is distinguishable from the signal of another marker in the set; and (d) is present in an amount capable of detecting said analyte at a range of concentrations that differs from the range of analyte concentrations detectable by other markers.

It will be seen therefore that the marker sets of the present invention may be used to extend the dynamic range of an assay. The methods of the invention may thus be considered as methods of increasing the dynamic range of an assay (for an analyte). Expressed another way, the methods of the present invention may be used to detect an analyte over a range of concentrations in a single sample, particularly a greater range, or to extend or increase the concentration range over which the analyte may be detected.

As will be described in more detail below, the marker may interact with the analyte directly or indirectly. Thus the marker need not bind directly to the analyte, but may interact indirectly, for example by binding to a molecule which itself binds directly or indirectly to the analyte (e.g. the marker may interact with (e.g. bind to) a binding partner for the analyte, which is itself bound to the analyte, or it may interact with (e.g. bind to) a further molecule which is carried by, or attached to, the binding partner for the analyte). It may even, as described further below, bind to a molecule which is generated as a result of interaction with the analyte. Generally speaking, however, in preferred embodiments the marker will, directly or indirectly (by one or more intermediaries), be "bound" to the analyte.

The marker may therefore be viewed as having or comprising a binding site, or binding domain, and a detectable site or domain (or alternatively put, a reporter domain or site). The binding site or domain may bind, directly or indirectly, to the analyte, or more generally to a molecule which is involved in, or generated in, the analyte-detection assay (i.e. it is a "target-interacting" or "target-binding" site or domain wherein the "target" may be viewed as the analyte, directly or indirectly, or as a molecule involved in any step of the analyte-detection assay (method) or generated in the analyte-detection method). The detectable site or domain is the domain or site which may give rise to the signal which is generated by the marker. Since, as noted above, the signals from different markers in a set may be distinguished from one another, the detectable site or domain will differ from marker to marker. In other words, each marker in the set may comprise a different detectable site or detectable domain. The detectable site or domain may be viewed as a "label", but it is not required that it is itself directly capable of giving rise to a signal i.e. it need not be a directly signal-giving label. Possible signal-generating means and labels are discussed further below. On the other hand, since it is required that the respective markers in a set cannot each simultaneously interact with the analyte, it will be understood that, generally speaking, they will interact at or with the same site (e.g. on the analyte or an intermediary moiety which binds to or otherwise interacts with the analyte or on any molecule with is involved in or generated in the analyte-detection method (reaction)). Thus, generally speaking, the binding site or domain of each marker in the set may advantageously be the same.

Of particular interest in the present invention are assays (i.e. methods for detecting an analyte) that utilise markers (reporter molecules) that generate a unique nucleic acid molecule as the detectable "signal". In other words the signal may arise from the unique nucleic acid molecule which is generated. In this respect, the nucleic acid molecule that results from the interaction between the marker and the analyte (i.e. the molecule which indicates that the analyte is present in the sample) may be detected itself or the signal nucleic acid molecule may be enhanced, e.g. by amplification, in order to generate a detectable and quantifiable signal. The nucleic acid molecule "signal" may be detected by any appropriate method known in the art, e.g. by incorporation of labelled nucleotides (e.g. fluorescent labels, radioactive labels, etc), hybridisation to labelled molecules etc as discussed in more detail below.

Hence, any method capable of measuring the presence of nucleic acids in a sample may be utilised in the methods of the present invention where the signal generated in the assay is a nucleic acid molecule, e.g. PCR, NASBA (Nucleic Acid Sequence-Based Amplification), LCR (Ligase chain reaction), SMAP (SMart Amplification Process), HDA (Helicase-Dependent Amplification).

Examples of assays that can yield a unique nucleic acid molecule as a signal are described below, but this is in no way intended to represent an exhaustive list.

A proximity assay relies on the principle of "proximity probing", wherein an analyte is detected by the binding of multiple (i.e. two or more, generally two or three) probes, which when brought into proximity by binding to the analyte (hence "proximity probes") allow a signal to be generated. Typically, at least one of the proximity probes comprises a nucleic acid domain (or moiety) linked to the analyte-binding domain (or moiety) of the probe, and generation of the signal involves an interaction between the nucleic acid moieties and/or a further functional moiety which is carried by the other probe(s). Thus signal generation is dependent on an interaction between the probes (more particularly by the nucleic acid or other functional moieties/domains carried by them) and hence only occurs when both the necessary (or more) probes have bound to the analyte, thereby lending improved specificity to the detection system. The concept of proximity probing has been developed in recent years and many assays based on this principle are now well known in the art. For example, proximity ligation assays (PLAs) rely on proximal binding of proximity probes to an analyte to generate a signal from a ligation reaction involving or mediated by (e.g. between and/or templated by) the nucleic acid domains of the proximity probes.

Thus, in a proximity assay proximity probes may be used, which bind to the analyte and have nucleic acid domains, or moieties, which interact in a proximity-dependent manner upon said analyte binding, for example via ligation or via hybridisation and extension, to form a detectable, preferably amplifiable, nucleic acid detection product by means of which said analyte may be detected.

Proximity-probe based detection assays, and particularly proximity ligation assays permit the sensitive, rapid and convenient detection or quantification of one or more analytes in a sample by converting the presence of such an analyte into a readily detectable or quantifiable nucleic acid-based signal, and can be performed in homogeneous or heterogeneous formats.

Proximity probes of the art are generally used in pairs, and individually consist of an analyte-binding domain with specificity to the target analyte, and a functional domain, e.g. a nucleic acid domain coupled thereto. The analyte-binding domain can be for example a nucleic acid "aptamer" (Fredriksson et al (2002) Nat Biotech 20:473-477) or can be proteinaceous, such as a monoclonal or polyclonal antibody (Gullberg et al (2004) Proc Natl Acad Sci USA 101:8420-8424). The respective analyte-binding domains of each proximity probe pair may have specificity for different binding sites (targets or target sites) on the analyte, which analyte may consist of a single molecule or a complex of interacting molecules, or may have identical specificities, for example in the event that the target analyte exists as a multimer. As described further below, the proximity probes may not bind directly to the analyte, but may bind indirectly via the intermediacy of a primary binding partner for the analyte. Thus the proximity probes may bind to a binding partner for the analyte, which binding partner binds directly to the analyte. Accordingly the target for the proximity probe may be a binding partner for the analyte and thus the target site to which the proximity probe binds may be on a binding partner for the analyte. It will be understood that in such a case, the proximity probes may in one embodiment have different binding sites (target sites) on the same binding partner (target), to allow them to bind in proximity to the binding partner. When a proximity probe pair come into close proximity with each other, which will primarily occur when both are bound to their respective "target" sites on the same analyte or target molecule, the functional domains (e.g. nucleic acid domains) are able to interact, for example, nucleic acid domains may be joined to form a new nucleic acid sequence e.g. by means of a ligation reaction, which may be templated by a splint oligonucleotide added to the reaction, said splint oligonucleotide containing regions of complementarity for the ends of the respective nucleic acid domains of the proximity probe pair, or by hybridisation of the end regions of the nucleic acid domains and then extension from one of the hybridised nucleic acids using the other as template. The new nucleic acid sequence thereby generated serves to report the presence or amount of analyte in a sample, and can be qualitatively or quantitatively detected, for example by realtime, quantitative PCR (q-PCR).

Alternatively, rather than being ligated to each other, the nucleic acid domains of the proximity probes when in proximity may template the ligation of one or more added oligonucleotides to each other, including an intramolecular ligation to circularise an added linear oligonucleotide, for example based on the so-called padlock probe principle, wherein analogously to a padlock probe, the ends of the added linear oligonucleotide are brought into juxtaposition for ligation by hybridising to a template, here a nucleic acid domain of the proximity probe (in the case of a padlock probe the target nucleic acid for the probe). Various such assay formats are described in WO 01/61037 and U.S. Pat. No. 6,558,928. As described in these documents, the padlock probe may be provided in one part. However, such padlock probes may be alternatively provided in two or more parts; in other words two or more oligonucleotides are provided which each hybridise to the nucleic acid domains of at least a pair of proximity probes such that their respective ends are brought into juxtaposition for ligation and two or more separate ligation events take place, each templated by a nucleic acid domain of a proximity probe.

Thus, rather than interacting together (i.e. directly) the nucleic acid domains may interact indirectly, e.g. via an interaction of each domain with a marker. For example each nucleic acid domain (e.g. both nucleic acid domains of a pair of proximity probes) may hybridise to a marker. In particular such a hybridisation of both (or more domains) may only become possible upon binding of the proximity probes to their target in proximity.

WO 97/00446 and U.S. Pat. No. 6,511,809 disclose a heterogeneous format for proximity ligation assays, i.e. the analyte is first immobilised to a solid substrate by means of a specific analyte-binding reagent.

Homogeneous proximity ligation assays (i.e., in solution) are disclosed in WO 01/61037, WO 03/044231, WO 2005/123963, Fredriksson et al (2002) Nat Biotech 20:473-477 and Gullberg et al (2004) Proc Natl Acad Sci USA 101: 8420-8424.

Although pairs of proximity probes are generally used, modifications of the proximity-probe detection assay have been described, in e.g. WO 01/61037 and WO 2005/123963, where three proximity probes are used to detect a single analyte molecule, the nucleic acid domain of the third probe possessing two free ends which can be joined (ligated) to the respective free ends of the nucleic acid domains of the first and second probes, such that it becomes sandwiched between them. In this embodiment, two species of splint oligonucleotide are required to template ligation of each of the first and second probes' nucleic acid domains to that of the third.

In a further modification described in WO 2007/107743 the splint oligonucleotide to template ligation of the nucleic acid domains of two proximity probes is carried on a third proximity probe.

As noted above, not all proximity assays are based on ligation. WO 2007/044903 discloses proximity probe-based assays for detecting analytes which rely on the formation and detection of a released nucleic acid cleavage product. Some of the described embodiments involve a probe comprised of an analyte-binding moiety and an attached enzyme, which enzyme acts on a nucleic acid moiety attached to the analyte-binding moiety of a second probe, resulting in the release of a detectable nucleic acid cleavage product.

Proximity probing reactions can also be performed by utilizing two free 3' ends, one on each proximity probe with weak complementarity, and when in proximity, a DNA polymerase can extend these ends by adding dNTPs thus forming a detectable DNA template as described in U.S. Pat. Nos. 7,306,904 and 6,511,809.

Analyte detection assays, including in some embodiments proximity probe-like reagents, wherein a polymerase enzyme attached to an analyte-binding moiety of one probe acts on a nucleic acid moiety attached to the analyte-binding moiety of a second probe, are described in WO 2009/012220. In these assays, the action of the "tethered" polymerase which is part of one of the probes of a probe pair results in the generation of a template, free in solution, which is susceptible to amplification by an added polymerase. Unlike the tethered polymerase, the added polymerase is only able to act on the template generated by the tethered polymerase, and not directly on the nucleic acid moiety of the non-polymerase-containing probe of the probe pair. The action of the added polymerase results in amplification of the generated template, the amplified copies being detectable and indicative of the presence of analyte in the sample, according to the proximity probing principle.

In addition to modification to the proximity-probe detection assay, modifications of the structure of the proximity probes themselves have been described, in e.g. WO 03/044231, where multivalent proximity probes are used. Such multivalent proximity probes comprise at least two, but as many as 100, analyte-binding domains conjugated to at least one, and preferably more than one, nucleic acid(s).

Immuno-PCR assays, e.g. as described in U.S. Pat. No. 5,665,539, also result in a nucleic acid molecule as a signal. Immuno-PCR assays use a single probe, as defined above, to detect an analyte which has been immobilised. The probe is captured onto the solid phase via its interaction with the analyte and the nucleic acid domain of the probe can be detected by an amplification reaction.

Oligonucleotide Ligation Assays, e.g. as described in Landegren et al. (1988 Science, Vol 241, Issue 4869, 1077-1080) represent a further type of assay that results in a unique nucleic acid molecule as the signal to be detected. In essence this is a specific method for the detection of known single nucleotide polymorphisms (SNPs) and is based on the joining of two adjacent oligonucleotide probes (Capture and Reporter Oligonucleotides) using a DNA ligase while they are annealed to a complementary DNA target (e.g. PCR product).

Rolling circle amplification using padlock probes, e.g. as described in U.S. Pat. No. 6,558,928, or indeed any circular nucleic acid molecule as a template can also be used to generate a unique nucleic acid molecule and can be useful in amplifying an existing "signal" nucleic acid molecule (e.g. generated from a proximity probe assay) or in the detection of a specific analyte, e.g. wherein the analyte is a nucleic acid molecule.

In one aspect of the invention, the signal that results from the interaction between the marker and the analyte is generated indirectly, i.e. the markers of the composition of the invention need not physically interact with the analyte. In other words, the marker may interact with an intermediate molecule that is capable of binding to the analyte. Thus, the marker may interact with, e.g. bind to, a primary binding partner for the analyte. In other words the binding site or domain of the marker may interact with, e.g. bind to, a primary binding partner for the analyte. In such an embodiment the marker may be viewed a secondary reagent (e.g. secondary binding partner) for the analyte. Alternatively, the marker may bind to a (further) molecule which is bound to, or otherwise associated with or provided by, the primary binding partner for the analyte. Such a molecule might be a nucleic acid molecule carried by, or provided on, the primary binding partner.

By way of example, a preferred aspect of the invention involves a proximity assay as described above, wherein the proximity probes interact with the analyte to generate a unique nucleic acid molecule. Such a nucleic acid molecule may represent the "target" to which the marker binds, i.e. with which it interacts. This interaction may generate the signal. Alternatively, the marker may interact with the nucleic acid domains of a pair (or set) of proximity probes, when such proximity probes have bound to the analyte in proximity, to generate the signal. In particular in this embodiment, the marker may interact with the nucleic acid domains of proximity probes to generate a unique nucleic acid molecule, from which the signal may be generated. By way of example, discussed in more detail below, the nucleic acid domains of the proximity probe may act as templates for ligation of a marker. In such embodiments of the invention, the unique nucleic acid molecule generated by the proximity probes, or more generally the nucleic acid molecule with which the markers interact, effectively becomes the analyte to be detected by the markers of the invention.

Thus, expressed in another way, in the methods and uses etc. of the invention as set out above (and further below) the "analyte" may alternatively be referred to as a "target".

According to one aspect of the present invention, a unique nucleic acid molecule generated by proximity probes may then be detected using the marker composition defined herein, thereby detecting the analyte indirectly. Alternatively, the marker composition may interact with the nucleic acid domains of the proximity probes to generate a nucleic acid molecule which is detected, thereby indirectly to detect the analyte. In such aspects of the invention, the marker composition comprises at least two types (varieties) of marker, which may each interact with its "target" nucleic acid molecule, for example a unique nucleic acid molecule generated by proximity probes, or the nucleic acid domains of the proximity probes. As noted above a marker of the invention comprises a detectable (or "reporter") domain, which may be viewed as a "label", although it need not itself be directly signal-giving—the signal may be generated through the use of directly signal-giving labels in downstream reactions. The variety of markers is derived from the nature of the "label" in the marker, i.e. the way in which the interaction between the marker and the nucleic acid molecule is detected. Thus, on interaction with said nucleic acid molecule each marker is able to generate a signal (i.e. the label becomes detectable) that is distinguishable from the other marker(s) in the assay. Furthermore, the different types of marker in the composition are present in a predefined ratio. (Thus in the methods, uses and compositions defined above each marker in a marker set may be defined as present in a pre-defined ratio). Hence, interaction with the unique nucleic acid molecule will therefore generate at least two distinguishable signals (detectable labels) and these signals will be proportionate to the predefined ratio of markers in the marker composition. Detection of said signals is therefore indicative of the amount of analyte present in the sample.

In one aspect of the invention, the markers in the above described embodiment may be differently labelled nucleic acid primers or probes, which bind to the same sequence in the nucleic acid molecule(s) with which the marker interacts (e.g. a unique nucleic acid molecule generated by proximity probes, or the nucleic acid domains of proximity probes), preferably with the same, or substantially the same, affinity. The labels may be, for instance, fluorescent molecules with different excitation and/or emission wavelengths, or distinguishable nucleotide sequences (e.g. tags or motifs), i.e. part of the primer/probe that cannot bind (hybridise) to the target nucleic acid molecule (the effective target analyte). When the markers interact with the target (e.g. unique) nucleic acid molecule, some aspect of the marker molecule must be altered, thereby generating signal to indicate that the marker has been in contact with said nucleic acid molecule. For example, the marker may be a template for an amplification reaction, and only after interaction with the nucleic acid molecule to be detected can the amplification reaction commence. Thus, in one embodiment of the invention, the primers/probes may be in the form of "padlock probes", as described herein. Thus, for example, each padlock probe "marker" may comprise (i) a common nucleotide sequence capable of hybridising to the nucleic acid molecule to be detected (e.g. the unique nucleic acid molecule generated by the interaction of the proximity probes which is representative of the amount of target analyte in the sample, or nucleic acid molecules represented by the nucleic acid domains of a set of proximity probes, when brought into proximity by binding of the proximity probes to the analyte) and (ii) a distinguishable or detectable nucleotide sequence (which may be unique), which may act as a label or a signal to be detected. Hence, the differently labelled padlock probes of the marker composition (marker set) will compete for the same binding site on the nucleic acid molecule. On interaction of the padlock probes with the nucleic acid molecule to be detected, the padlock probes may be ligated (e.g. by a ligase enzyme) to form a circular nucleic acid molecule, i.e. the markers are altered only on interaction with the target analyte. Under the conditions of the assay the markers (padlock probes) can be amplified only on circularisation, e.g. by rolling-circle amplification, and the amplification product, which comprises a nucleotide sequence that is distinctive or representative of (e.g. unique to) the type of padlock probe used as the template, may be detected. As each type of padlock probe "marker" in the marker composition (or marker set) comprises a different label, detection of each label will provide a different measurement of the same target/analyte (in this case, the nucleic acid molecule with which the marker interacts, or in particular hybridises, e.g. the unique nucleic acid molecule or a nucleic acid domain of the proximity probe). Preferably at least one of the measurements will be a non-saturated signal, thereby enabling quantification of the analyte in the sample.

It will be apparent to the skilled person that the methods of the invention are applicable to any assay that utilises a reporter molecule to detect an analyte and in particular wherein the detection involves the production of a unique nucleic acid molecule. Thus, for example, the embodiments of the invention described above, i.e. where the marker set of the invention comprises nucleic acid molecules, can be used to extend the dynamic range of any method used to detect a nucleic acid molecule, i.e. where the nucleic acid molecule is the analyte or where the presence of an analyte is "converted" (i.e. transposed) into a nucleic acid molecule to be detected instead of the analyte.

In a further embodiment of the invention, and an alternative example of an assay wherein the signal that results from the interaction between the marker and the analyte is generated indirectly, is immuno-RCA and Immuno-PCR. In this aspect of the invention, the immuno-RCA or Immuno-PCR probe, which comprises an analyte-binding domain (i.e. an element that binds to the analyte) and a nucleic acid domain, is first allowed to interact with the analyte. Following interaction with the analyte, the marker composition as defined herein is added to the sample and under conditions that would enable the generation of the distinguishable signals, e.g. differently labelled padlock probes will interact with the nucleic acid domain of the immuno-RCA or Immuno-PCR probe, which can then be detected as described above.

In an alternative embodiment, immuno-PCR or Immuno-RCA probes may form the markers of the invention. In this embodiment, the probes would comprise a common analyte-binding domain and different nucleic acid domains, e.g. 20% of the probes would comprise nucleic acid domain A and 80% of the probes would comprise nucleic acid domain B. Detection of each of the nucleic acid domains by any appropriate means known in the art (and as described further below) would yield at least two distinguishable signals, thereby enabling the detection and/or quantification of the analyte in question.

In yet a further embodiment of the invention, it will be evident to a person of skill in the art that sets of proximity probes may be used as the marker sets (compositions) as described herein. Whilst the proximity assays described above require at least two proximity probes, and therefore two analyte-binding sites, it is possible to substitute at least one of the proximity probes with a composition of differently labelled proximity probes in a predefined ratio, i.e. making at least one of the proximity probes a set of markers in accordance with the invention. For instance, the proximity probe marker composition may comprise at least two probes with a common analyte-binding domain (i.e. so that they compete for the same analyte-binding site) and different nucleic acid domains, as described above. When the proximity probes are allowed to interact with the analyte, two unique nucleic acid molecules (i.e. signals) will be generated in different proportions according to the predefined ratio of the proximity probe marker composition. Said signals may be detected by any appropriate means, e.g. amplification, hybridisation, incorporation of labelled nucleotides etc.

It will be understood that the methods described herein are advantageously useful in extending the dynamic range of single molecule amplification methods. In particular, the methods of the invention find utility in all amplification methods utilizing single molecule read-outs. For example, a preferred embodiment of the invention concerns the application of the described methods in digital PCR, i.e. any method that results in the generation of a unique nucleic acid molecule that can be amplified to yield a signal may be used in a digital PCR assay. As described above, a significant limitation in digital PCR methods results from inefficiency due to over-dilution of the sample. Hence, methods of the invention to extend the dynamic range of an assay are especially useful in digital PCR assays because a useful signal may be obtained without heavily diluting the sample.

In a particularly preferred embodiment of the invention, the method of the invention utilises an Oligonucleotide Ligation Assay (OLA) to generate the substrate for a digital PCR. Typically, the OLA is utilised to detect different alleles of a single gene, however it is evident in the context of the present invention, that this assay could be, for example, used to detect any target molecule by using differentially labelled oligonucleotide probes present in a predefined ratio. Typically, an OLA comprises a capture probe (capture oligonucleotide) for each allele of the target molecule to be detected and a reporter probe (reporter oligonucleotide) that is common to the target nucleic acid molecule to be detected. The capture probe is capable of hybridising to an allele of the target sequence and is labelled to provide a "signal". The reporter probe is complementary to the target DNA sequence immediately downstream (3') of the site to which the capture probe anneals (hybridizes). The reporter probe is modified with a phosphate at its 5' end to enable ligation to occur. Thus, when the probes and target are brought together under conditions that allow them to interact and ligate together (e.g. in the presence of a ligase enzyme) the capture and reporter probes will be ligated, but only when there is no mismatch in the hybridising sequence of the capture probe and the target nucleic acid, e.g. where different alleles are present in the sample (the ligase enzyme is selected on the basis that it cannot ligate mismatched sequences).

Thus, in the context of the present invention, each capture probe may be provided as a composition of differently labelled capture probes in a predefined ratio. The label could any convenient label as described herein. However, in the digital PCR embodiment, the label will be preferably a distinct or distinguishable (e.g. unique) nucleic acid sequence (or domain), as described elsewhere herein, i.e. a sequence or domain that does not hybridise to the target nucleic acid molecule. Hence, the OLA will result in differentially labelled nucleic acid molecules proportional to the ratio of the differently labelled capture probes present in the marker composition (for each allele, if more than one allele is being detected). Expressed in another way, the OLA may be seen as a method of providing a labelled representation of nucleic acid molecules in a sample. These differentially labelled nucleic acid molecules may be utilised in a digital PCR. An example of OLA is shown in FIG. 6.

Hence, this embodiment of the invention could be considered as a method of generating a representative sample (i.e. a cross-section or proportion) of nucleic acid molecules in a complex sample, i.e. a method of labelling a proportion of nucleic acids in a sample.

It will be clear from the above described embodiments that the marker composition of the invention can be applied to any method that relies on labels to obtain quantitative data. Hence, any variations of the above described methods may be adapted for use in the methods of the invention. It will also be apparent that the methods of the invention are not limited to methods where the "signal" is a nucleic acid molecule, or is generated from a nucleic acid molecule. For example, proximity assays may utilise labels other than nucleic acid molecules, e.g. enzyme/substrate. Thus, the proximity probe marker composition described above could comprise probes comprising a common analyte-binding domain and different enzyme substrates that result in different products on interaction with the enzyme coupled to the probe of the "common" proximity probe.

Accordingly, one preferred aspect of the invention provides a method of detecting an analyte in a sample wherein said method comprises:

(i) contacting said sample with at least one set of markers, wherein said set comprises at least two markers, wherein each marker:
  (a) is capable of interacting with said analyte and generating a detectable signal;

(b) cannot interact with the analyte simultaneously with another marker in the set;

(c) generates a signal that is distinguishable from the signal of another marker in the set; and (d) is present in an amount capable of detecting the analyte at a range of concentrations that differs from the range of analyte concentrations detectable by other markers, (ii) allowing said markers to interact with said analyte; and (iii) detecting said signal.

Alternatively viewed a preferred aspect of the present invention can be seen as a method of obtaining a non-saturated signal in an assay for detecting an analyte in a sample wherein said method comprises:

(i) contacting said sample with at least one set of markers, wherein said set comprises at least two markers, wherein each marker:

(a) is capable of interacting with said analyte and generating a detectable signal;

(b) cannot interact with the analyte simultaneously with another marker in the set;

(c) generates a signal that is distinguishable from the signal of another marker in the set; and (d) is present in an amount capable of detecting a range of concentrations that differs from the range of analyte concentrations detectable by other markers, (ii) allowing said markers to interact with said analyte; and (iii) detecting said signal.

Whilst not wishing to be bound by theory, it is believed that the methods of the invention rely upon the competition between the markers in the marker set (composition) of the invention. As the each of the markers from a single "set" or "composition" must interact with the same binding site in order to generate a signal, the marker present in the greatest proportion will interact more frequently than the other marker(s). Hence, the signal generated by each of markers will be proportional (although not necessarily directly proportional) to the ratio of marker present in the marker composition. As described above, depending on the amount of analyte in the sample, at least one of the markers will generate a non-saturated signal.

In one embodiment of the invention more than one analyte may be detected in a single assay. In this respect, multiple sets of markers are contacted with the sample. Each set of markers comprises at least two markers as described elsewhere herein. By more than one analyte is meant at least 2, 3, 4, 5, 10, 20, 50, 100 etc different analytes.

As described above, the markers of the invention may interact directly or indirectly with the analyte of the invention. Where the markers interact indirectly, the method of the invention preferably comprises at least one step before part (i) as described above, wherein a molecule or binding partner which binds to the target analyte is first added to the sample (or added at the same time as the marker composition) and allowed to interact with the target analyte. This binding partner (analyte-binding molecule or moiety) is said to be an intermediary molecule (binding partner). Preferably the marker of the invention is capable of binding to the intermediary molecule or otherwise interacting with a molecule or domain (a signal) generated by the intermediary molecule. Particularly, the analyte-binding molecule or the intermediary binding partner is a specific binding partner for the analyte. A binding partner is any molecule or entity capable of binding to its target, e.g. target analyte, and a specific binding partner is one which is capable of binding specifically to its target (e.g. the target analyte, e.g. a part of, i.e. a target on the analyte), namely that the binding partner binds to the target (e.g. analyte) with greater affinity and/or specificity than to other components in the sample. Thus binding to the target analyte may be distinguished from non-target analytes; the specific binding partner either does not bind to non-target analytes or does so negligibly or non-detectably or any such non-specific binding, if it occurs, may be distinguished. The binding between the target analyte and its binding partner is typically non-covalent.

Multiple intermediary binding steps may be included before (or at the same time as) step (i) as described above, such that the markers of the invention are capable of interacting with at least one of the intermediary molecules and generating a detectable signal, thereby providing a means of indirectly detecting the target analyte.

The "analyte" may be any substance (e.g. molecule) or entity it is desired to detect by the method of the invention. The analyte may be viewed as the "target" of the assay method of the invention. Hence, where the target analyte is first interacted with an intermediary binding molecule, the intermediary molecule or any molecule (e.g. signal-generating molecule) generated by said intermediary molecule may effectively become the "target analyte", or the target of the markers.

The analyte may accordingly be any biomolecule or chemical compound it may be desired to detect, for example a peptide or protein, or nucleic acid molecule or a small molecule, including organic and inorganic molecules. In a preferred embodiment the analyte is not a nucleic acid molecule, i.e. the analyte is a non-nucleic acid analyte. However, a non-nucleic acid analyte may in some embodiments comprise a nucleic acid component, i.e. where the analyte is not solely a nucleic acid molecule (the analyte does not consist of one or more nucleic acid molecules). For example, a non-nucleic acid analyte may be a complex of protein and nucleic acid, i.e. wherein at least one target site of the analyte is a non-nucleic acid target site, e.g. a protein. The analyte may be a cell or a microorganism, including a virus, or a fragment or product thereof. It will be seen therefore that the analyte can be any substance or entity for which a specific binding partner (e.g. an affinity binding partner) can be developed. All that is required is that the analyte is capable of binding at least one binding partner, i.e. it comprises at least one site, a target, to which a binding partner may interact, e.g. bind, specifically. In a preferred embodiment of the invention the analyte is capable of binding at least two binding partners, e.g. the analyte-binding domains of at least two proximity probes.

Proximity probe-based assays have found particular utility in the detection of proteins or polypeptides. Analytes of particular interest may thus include proteinaceous molecules such as peptides, polypeptides, proteins or prions or any molecule which includes a protein or polypeptide component, etc., or fragments thereof. The analyte may be a single molecule or a complex that contains two or more molecular subunits, which may or may not be covalently bound to one another, and which may be the same or different. Thus in addition to cells or microorganisms, such a complex analyte may also be a protein complex or protein interaction. Such a complex or interaction may thus be a homo- or heteromultimer. Aggregates of molecules, e.g. proteins may also be target analytes, for example aggregates of the same protein or different proteins. The analyte may also be a complex between proteins or peptides and nucleic acid molecules such as DNA or RNA. Of particular interest may be the interactions between proteins and nucleic acids, e.g. regulatory factors, such as transcription factors, and DNA or RNA.

All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared or they may be prior-treated in any convenient way e.g. for storage.

Representative samples thus include any material which may contain a biomolecule, or any other desired or target analyte, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, blood cells, urine, faeces, cerebrospinal fluid or any other body fluids (e.g. respiratory secretions, saliva, milk, etc), tissues, biopsies, cell cultures, cell suspensions, conditioned media or other samples of cell culture constituents, etc. The sample may be pre-treated in any convenient or desired way to prepare for use in the method of the invention, for example by cell lysis or purification, isolation of the analyte, etc.

A preferred aspect of the invention is therefore a method of obtaining a non-saturated signal in an assay for detecting an analyte in a sample. A non-saturated signal may be defined as a signal that is not at or beyond the maximum threshold of detection, i.e. a non-saturated signal is at a level where a further increase in the signal may still be detected (and quantified). Hence, in the context of the present invention two signals that are both saturated may not be distinguished from each other, even though they may represent different levels of analyte.

As noted above, the markers of the invention comprise two domains, a binding domain and a detectable or reporter domain. Preferably the binding domain and the detectable/reporter domain are coupled or linked. This link may be covalent or non-covalent.

In preferred embodiments, the binding domain of the markers is capable of interacting specifically with the target analyte either directly or indirectly, e.g. via an intermediary molecule. Thus, the binding domain binds to the target (e.g. analyte) with greater affinity and/or specificity than to other components in the sample. Thus binding to the target may be distinguished from non-target; the binding domain either does not bind to non-target molecules or does so negligibly or non-detectably or any such non-specific binding, if it occurs, may be distinguished. The binding between the target (analyte) and its binding partner is typically non-covalent.

In a preferred embodiment of the invention, the binding domain of the markers of the invention is a nucleic acid molecule, preferably an oligonucleotide. In a particularly preferred embodiment of the invention, the binding domain of the markers is part of a padlock probe or circular oligonucleotide, as defined elsewhere herein.

The reporter (or detectable) domain of the markers comprises or may give rise to a detectable signal, i.e. it comprises a label that can be detected specifically (e.g. that can be distinguished from a label of a different marker). Said signal may be produced directly or indirectly. A direct signal is one that does not require enhancement or manipulation in order to be detected. For example, the reporter domain may comprise signal (label) that may be selected from, but is not limited to, any one or more of fluorophores, fluorescent proteins, radioactive isotopes, colorimetric detection labels such as chromogens, magnetic particles, particles such as carbon, silver or gold, quantum dots, enzymes. Thus, the label of the marker may be directly "signal-giving". Alternatively, the signal may be indirect, by which is meant the label in or of the marker must be manipulated or enhanced to make it detectable, i.e. the reporter domain of the marker is capable of generating a detectable signal. For example, the reporter domain may comprise a nucleic acid molecule, e.g. an oligonucleotide, which may require some further treatment in order to generate a detectable signal. For example, the nucleic acid molecule may be amplified, e.g. by any suitable method known in the art (e.g. PCR) and said amplification product may be detected.

Thus, the markers used in the methods of the invention will depend on the nature of the analyte or any intermediary molecule. In a preferred embodiment of the invention the markers are oligonucleotides, preferably padlock probes or circular oligonucleotides as defined elsewhere herein. Thus, in a particularly preferred embodiment, both the binding domain and the reporter domain comprise nucleic acid molecules, preferably these form two parts of the same nucleic acid molecule.

A set of markers (or a marker composition) comprises at least two types of marker as defined above, wherein the binding domain of the marker is the same as the other markers in the set, but the reporter domain of the markers in the set is different. For example, the binding domain may comprise a proteinaceous analyte-binding domain, e.g. an antibody, and the reporter domain may comprise fluorophores with different excitation and emission properties. In a preferred embodiment, the reporter domain of the markers is of the same type, e.g. different fluorophores, nucleic acid molecules with unique sequences etc. such that they can be detected using the same detection methods/equipment/instrumentation etc.

The binding domain of the markers is selected such that the differently labelled markers cannot simultaneously bind to the analyte. In this respect, the binding domain of the markers must bind to at least part of the same part of the target analyte (or the intermediary molecule, i.e. the effective analyte). In other words, the binding domains of the markers must overlap sufficiently to prevent both markers binding to the target analyte or intermediary molecule at the same time. In a preferred embodiment the binding domain of the markers have the same or substantially the same binding affinity and/or specificity for the target analyte. In a particularly preferred embodiment the binding domain of the markers is the same, e.g. where in the binding domain is an antibody, the same antibody is used and is simply coupled to different reporter domains (in predefined ratios). Similarly, where the binding domain is a nucleic acid molecule, the domain preferably comprises the same nucleotide sequence, i.e. sequences that share at least 80% sequence identity, preferably at least 85, 86, 87, 88, 89, 90, 91, 92, 93, 94, 95, 96, 97, 98, 99 or 100% sequence identity. Sequence identity may be determined by any appropriate method known in the art, e.g. the using BLAST alignment algorithm.

The signal generated from the reporter domain must be distinguishable from the signal of another marker in the sample. Hence, not only must reporter domains of markers in the same marker set be different from each other, but also reporter domains of different marker sets must be different from each other. By distinguishable is meant that each signal/label may be measured separately to the other signals present in the sample, preferably with little or no overlap in signal. For example, where the reporter domain is a nucleic acid domain, it is preferable that the nucleotide sequences of the domains have less than 80% sequence identity, preferably less than 70, 65, 60, 55, 50, 45, 40, 30, 20 or 10% sequence identity.

Each marker in the method of the invention is present in an amount capable of detecting the analyte (directly or indirectly) at a range of concentrations that differs from the range of analyte concentrations detectable by other markers in the sample. As described above, each marker in any set of markers must have the same or substantially the same binding properties as the other markers in the set. Hence, if the markers were present at the same concentration as each other, it would be expected that each marker would be capable of detecting the same analyte concentration range. Thus, in order to extend the dynamic range of an assay, it is essential that each marker in the set of markers is present in different amounts, i.e. the marker set comprises a predefined ratio of differently labelled markers (markers with different reporter domains). The predefined ratio will be dependent on the nature of the assay and the likely concentration range of the analyte in the sample. However, examples of useful ratios may be selected from, but are in no way limited to, any one of at least 1:2, 1:3, 1:4, 1:5, 1:10, 1:25, 1:50, 1:100, 1:200, 1:300, 1:500, 1:1000, 1:5000, 1:10000, 1:50000, 1:100000, 1:500000, 1:1000000 etc. It is contemplated that each marker set will comprise at least two markers, e.g. 2, 3, 4, 5, 6, 7, 8, 9, 10, 20, 50, 100 etc and thus the predefined ratio will be determined accordingly. For example, where the marker set comprises three markers, the ratio could be 1:5:25, 1:10:100, 1:100:1000 etc, for four markers the ratio could be 1:2:5:10, 1:5:25:100, 1:10:100:1000, 1:100:500:5000 and so on.

The term "detecting" is used broadly herein to include any means of determining the presence of the analyte (i.e. if it is present or not) or any form of measurement of the analyte. Thus "detecting" may include determining, measuring, assessing or assaying the presence or absence or amount or location of analyte in any way. Quantitative and qualitative determinations, measurements or assessments are included, including semi-quantitative. Such determinations, measurements or assessments may be relative, for example when two or more different analytes in a sample are being detected, or absolute. As such, the term "quantifying" when used in the context of quantifying a target analyte(s) in a sample can refer to absolute or to relative quantification. Absolute quantification may be accomplished by inclusion of known concentration(s) of one or more control analytes and/or referencing the detected level of the target analyte with known control analytes (e.g., through generation of a standard curve). Alternatively, relative quantification can be accomplished by comparison of detected levels or amounts between two or more different target analytes to provide a relative quantification of each of the two or more different analytes, i.e., relative to each other.

As discussed above, in one preferred embodiment of the invention the markers may comprise proximity probes. Alternatively, the "signal" generated by a proximity assay may be treated as the effective target analyte of the present invention, i.e. the proximity probes may act as the intermediary molecule(s) described above. Proximity assays and probes are well described in the literature and such probes are known to comprise two components which can be defined similarly to the markers of the present invention, i.e. an analyte-binding domain and a functional (reporter) domain. Hence, proximity probes are in effect detection probes which bind to the analyte (via the analyte-binding domain), the binding of which may be detected (to detect the analyte) by means of detecting the interaction which occurs between the functional domains thereof upon such binding.

The analyte-binding domain may be any binding partner for the target analyte, and it may be a direct or indirect binding partner therefor. Thus it may bind to the target analyte directly (i.e. bind to a target site on the analyte), or as discussed above the proximity probes may also bind indirectly via an intermediary molecule or binding partner which binds to the target analyte, the analyte-binding domain binding to said intermediary molecule (binding partner) (i.e. binding to a target site on the intermediary molecule). Particularly, the analyte-binding domain or the intermediary binding partner is a specific binding partner for the analyte. In some embodiments, e.g. where the proximity probes bind to the analyte or binding partner to provide a nucleic acid "target" with which the markers can interact, the target- or analyte-binding domain of each proximity probe may bind to the analyte (e.g. a target site on the analyte) or to a binding partner that is bound to the analyte (e.g. a target site on the binding partner). Hence in some embodiments, the target-binding domain of each proximity probe may be bound to their respective target sites on the analyte. In other embodiments, the target-binding domain of each proximity probe may be bound to respective sites on one or more binding partners. For instance, the analyte may interact with a single binding partner comprising more than one target site, wherein the target-binding domain of each proximity probe interacts with a different target site on the binding partner. Alternatively, the analyte may interact with more than one binding partner (i.e. each binding partner interacting with a different target site on the analyte), wherein the target-binding domain of each proximity probe interacts with a target site on one of the binding partners. In a further embodiment, the target-binding domain of one proximity probe may interact with a target site on the analyte and another proximity probe may interact with a target site on a binding partner of the analyte. It will be evident that other combinations are possible, particularly when the methods of the invention use more than two proximity probes and such combinations form embodiments of the invention.

A binding partner is any molecule or entity capable of binding to its target, e.g. target analyte (i.e. a site on, or a part of, the analyte), and a specific binding partner is one which is capable of binding specifically to its target (e.g. the target analyte), namely that the binding partner binds to the target (e.g. analyte) with greater affinity and/or specificity than to other components in the sample. Thus binding to the target analyte may be distinguished from non-target analytes; the specific binding partner either does not bind to non-target analytes or does so negligibly or non-detectably or any such non-specific binding, if it occurs, may be distinguished. The binding between the target analyte and its binding partner is typically non-covalent.

The analyte binding domain may be selected to have a high binding affinity for a target analyte. By high binding affinity is meant a binding affinity of at least about $10^{-4}$ M, usually at least about $10^{-6}$ M or higher, e.g., $10^{-9}$ M or higher. The analyte binding domain may be any of a variety of different types of molecules, so long as it exhibits the requisite binding affinity for the target analyte when present as part of the proximity probe. In other embodiments, the analyte binding domain may be a ligand that has medium or even low affinity for its target analyte, e.g. less than about $10^{-4}$ M.

Hence, the analyte-binding domain of the proximity probe (and thus a marker of the invention) may be any molecule capable of selectively binding to a target molecule. For example, the binding domain may be selected from a protein, such as a monoclonal or polyclonal antibody, lectin, soluble cell surface receptor, combinatorially derived protein from phage display or ribosome display, peptide, carbohydrate, nucleic acid, such as an aptamer, or combinations thereof. In a preferred embodiment of the invention, the analyte binding domain is a protein, preferably an antibody or derivative or fragment thereof.

The functional (reporter) domain of the proximity probe (and thus a marker of the invention) may be any molecule capable of interacting specifically with the functional domain of another proximity probe, wherein said interaction results in a detectable signal. Hence, the functional domains could be selected from an enzyme and substrate, binding proteins, nucleic acid molecules, fluorophores, fluorescent proteins etc. In a particularly preferred embodiment of the invention, the functional (reporter) domain of the proximity probes (and markers) is a nucleic acid molecule.

Accordingly, where the functional domain is a nucleic acid molecule, the probes may be viewed as nucleic acid-tagged affinity ligands or binding partners for the analyte, the analyte-binding domain being the affinity binding partner, and the nucleic acid domain a nucleic acid tag. The nucleic acid domain is coupled to the analyte-binding domain and as noted below, this "coupling" or connection may be by any means known in the art, and which may be desired or convenient and may be direct or indirect, e.g. via a linking group. Examples of the way in which a protein may be coupled to a nucleic acid are described in detail below.

Where the binding domain of the marker or (proximity) probe of the present invention is a proteinaceous molecule the analyte-binding domain may be a small peptide molecule or a larger polypeptide or protein. A peptide may, for example range in size from about 5 to about 100 amino acid residues, usually from about 5 to about 50 residues and more usually from about 10 to about 30 residues. By large polypeptide or protein is meant a molecule ranging in size from about 100 amino acid residues or greater. Of particular interest as analyte-binding domains are antibodies, as well as binding fragments and derivatives or mimetics thereof. Where antibodies are the analyte-binding domain, they may be derived from polyclonal or monoclonal compositions such that the analyte-binding domain may be either a monoclonal or polyclonal antibody. In yet other embodiments, the affinity-binding domain is an antibody fragment or derivative or mimetic thereof, where these fragments, derivatives and mimetics have the requisite binding affinity for the target analyte. Examples of antibodies, antibody fragments, mimetics and derivatives thereof are described below and the present invention contemplates the affinity-binding domain may be any type of these molecules, provided they have the requisite binding affinity for the target analyte.

Importantly, the analyte-binding domain will be one that includes a moiety that can be covalently attached to the functional (e.g. nucleic acid) domain without substantially abolishing the binding affinity of the analyte-binding domain to its target analyte.

In one embodiment of the invention the markers may be oligonucleotides, e.g. primers or probes. In a preferred embodiment of the invention, the oligonucleotide markers may be circularised by a ligation reaction (i.e. akin to a padlock probe as described above). For instance, one, two, three or more oligonucleotides may be provided such that they can be ligated to form a circle oligonucleotide. In an alternative embodiment the oligonucleotide may be provided as a "preformed circle", i.e. a nucleic acid molecule without ends, such that no ligation is required (as described in US 2004/0248103). Thus, in a particularly preferred embodiment of the invention the oligonucleotide markers are used in combination with a proximity probe assay to detect a target analyte. By way of example one or more of the nucleic acid domains of a pair of proximity probes, which are attached to the analyte-specific binding moieties of the respective probes, may have complementarity, to the 5' and 3' ends, of the differently labelled added linear oligonucleotide markers (akin to "padlock probes"), wherein the different label (i.e. the reporter domain) is a distinguishable or distinctive e.g. unique nucleotide sequence. Thus for example a nucleic acid domain of one proximity probe may have complementarity to both the 5' and 3' ends of the marker oligonucleotide. The nucleic acid domain of the other proximity probe may have complementarity to another region of the oligonucleotide marker (i.e. a region which is not at the 5' or 3' ends, e.g an intermediate or "internal" region). When both probes of the proximity probe pair are brought into proximity, e.g. due to binding to the same analyte, the nucleic acid domains of the respective probes are able to hybridise to the respective parts of the added oligonucleotide markers. The nucleic acid domain with complementarity to the 5' and 3' ends of the added oligonucleotides templates the juxtaposed hybridisation, and ligation (on addition of an appropriate ligase), of said ends, resulting in circularisation of the added oligonucleotide markers. In an embodiment where the oligonucleotide marker is provided as a preformed circle, it will be evident that the region of complementarity to the nucleic acid domain of the proximity probe and the reporter domain (i.e. the distinguishable or distinctive, e.g. nucleic acid sequence) will both be "internal" sequences. The circularised (or preformed circle) oligonucleotide markers are then detected by rolling circle amplification (RCA), for example using the unique nucleic acid domain (i.e. the reporter domain for each marker) as primer binding site. However, a primer site common to both oligonucleotide markers may be used to amplify both signals. Alternatively and advantageously, the 3' end of one of the nucleic acid domains of a proximity probe may function as a primer. In the case of the embodiment described above this would be the non-templating nucleic acid domain which is hybridised to the marker (at the "intermediate" or "reporter domain" region)—this is well-known and widely described in the proximity probe art, e.g. as cited above and below. Upon the addition of an appropriate polymerase (and if necessary primer(s)), the presence of analyte in the sample may be detected by an rolling circle amplification (RCA) of the circularised (or preformed circle) oligonucleotides. The concatemeric RCA products, which can only be formed when the proximity probes bind in proximity, i.e. to form a template for the hybridisation or the oligonucleotide and/or ligation reaction, provides the marker "signal" for detection of the analyte. Said signal may be detected by any appropriate means known in the art (see below for further examples) and as taught in U.S. Pat. No. 7,320,860, e.g. by hybridisation of labelled probes to the reporter domain sequence, which is repeated throughout the concatemeric RCA products.

It will be appreciated that each oligonucleotide marker can be replaced by two oligonucleotides which may be ligated together to form a circle (such a ligation may be templated by one or both nucleic acid domains of the proximity probes). For example the binding domain and the reporter domains of the markers may be on separate oligonucleotides. In such a case, a constant amount of the binding domain oligonucleotide may be added to the assay and a predetermined ratio of the reporter molecule oligonucleotides will be added to achieve the at least two markers which are present in an amount capable of detecting the analyte at a range of concentrations that differs from each other.

It will be further appreciated that the proximity probes can be replaced by any "probe" that comprises an analyte-binding domain coupled to a nucleic acid domain, i.e. any molecule that can bind specifically to the analyte comprising also a nucleic acid domain capable of, e.g. templating a ligation reaction.

Accordingly, one aspect of the invention provides a method of detecting an analyte in a sample wherein said method comprises:

(i) contacting said sample with at least two probes comprising an analyte-binding domain coupled to a nucleic acid domain (in particular such that said nucleic acid domains may be allowed to interact directly or indirectly when the probes have bound in proximity to the analyte, said analyte-binding domains being bound either to a target on the analyte or a target on a binding partner for the analyte);

(ii) further contacting said sample with at least one set of markers, wherein said set comprises at least two markers, wherein each marker:
  (a) is capable of interacting with said nucleic acid domains (where said probes have bound to the analyte in proximity) to form a nucleic acid molecule from which a detectable signal is generated, or with a nucleic acid molecule generated by interaction of said nucleic acid domains;
  (b) cannot interact with said nucleic acid domains simultaneously with another marker in the set;
  (c) generates a signal that is distinguishable from the signal of another marker in the set; and
  (d) is present in an amount capable of detecting the (interaction of the) nucleic acid domains, and therefore the analyte, at a range of concentrations that differs from the range of nucleic acid domains, and therefore analyte, concentrations detectable by other markers;

(ii) allowing said markers to interact with said nucleic acid domains; and (iii) detecting said signal.

Thus, in one embodiment the probe is a proximity probe or an immuno-PCR or immuno-RCA probe. Where the probe is a proximity probe, the probe may be allowed to interact so as to form a nucleic acid molecule with which the markers of the marker set can interact. In a particularly preferred embodiment the proximity probes interact in a proximity ligation assay or a proximity extension assay.

In one embodiment, where the proximity probes are the markers of the invention, the nucleic acid domains of the proximity probes may be ligated to form a circular nucleic acid molecule which may be amplified, e.g. by rolling circle amplification, to generate the "signal". In essence the nucleic acid domains of the proximity probes must have two free ends such that the domains may be ligated together to generate the circular nucleic acid molecule. Such a ligation may be, for example, templated by "splint" oligonucleotides, which may be added to the reaction separately or hybridised to the nucleic acid domain of the proximity probe. Numerous variations of the assay will be apparent to a person of skill in this field and are described in detail in US 2004/0248103. In the context of the present invention, one of the probes would be provided at a constant concentration and the other probe would be provided as a composition of differently labelled proximity probes (each with a different nucleic acid domain) in a predefined ratio, i.e. making at least one of the proximity probes a set of markers in accordance with the invention, as described above.

In an alternative embodiment, the proximity probes which comprise nucleic acid domains with two free ends may act simply as a hybridisation target for the above described "preformed circle" oligonucleotides. Thus, in the context of the present invention, the preformed circle oligonucleotides are the markers of the invention, wherein each oligonucleotide marker comprises a distinguishable or distinctive nucleotide "reporter domain" sequence and the different markers are provided in a predefined ratio. Alternatively and advantageously, the 3' end of one of the nucleic acid domains of a proximity probe may function as a primer. In the case of the embodiment described above the nucleic acid domain may be hybridised to the marker at the "reporter domain" or "binding domain" region, or to a part of the "binding domain".

In a particularly preferred embodiment the preformed circle oligonucleotides are capable of hybridising to the nucleic acid domain of only one of the proximity probes (the proximity probe that does not act to prime rolling circle amplification), under the specific reactions conditions, when the probes are not in proximity, i.e. when the probes are not all bound to their respective target (being either the analyte or a binding partner for the analyte). In particular, the preformed circle oligonucleotide markers are not capable of hybridising to the nucleic acid domain that acts as a primer for rolling circle amplification unless the proximity probes are bound in proximity. Alternatively viewed, the nucleic acid domain of the proximity probe that is capable of priming rolling circle amplification can act as a primer when the proximity probes are bound in proximity.

Thus, when the proximity probes are bound in proximity, the preformed circle oligonucleotide bound to the nucleic acid domain of a first proximity probe (the non-priming nucleic acid domain) may hybridise with the nucleic acid domain of a second proximity probe (the priming nucleic acid domain) which functions as a primer for rolling circle amplification, thereby enabling or facilitating the interaction between the nucleic acid domains of the proximity probes. Thus, the nucleic acid domain of said first proximity probe may be seen to stabilise the interaction between the marker and the nucleic acid domain of said second proximity probe (or alternatively, to stabilise the interaction between the nucleic acid domains of the proximity probes).

In a preferred embodiment the nucleic acid domain of said first proximity probe cannot function as a primer. Thus, a detectable nucleic acid molecule (i.e. a signal) is generated (e.g. rolling circle amplification can proceed) only if said first and second proximity probes are bound in proximity. The nucleic acid molecule that is generated is an extension of the nucleic acid domain of said second proximity probe, i.e. it is tethered or coupled to the analyte-binding domain of said second proximity probe. This is particularly advantageous in hetereogeneous assays, i.e. wherein the analyte is immobilised, or in in situ assays, e.g. on a cellular or tissue sample, thereby enabling the nucleic acid molecule generated by the rolling circle amplification reaction to act as a positional marker for the analyte, e.g. in microscopy (see the Examples).

Thus, in a preferred embodiment the binding domain (or a first part of the binding domain) of the preformed circle oligonucleotides (the markers of the invention) hybridises strongly (e.g. specifically) to the nucleic acid domain of a first the proximity probe and the binding domain (or a second part of the binding domain) hybridises weakly (e.g. transiently) with the nucleic acid domain of a second proximity probe. Strong hybridisation may be characterised as being capable of hybridising to the nucleic acid domain of said first proximity probe even when the proximity probes are not bound in proximity, i.e. the hybridisation is not reliant on the probes being bound to the target analyte in proximity. Weak hybridisation may be characterised as being capable of hybridising to the nucleic acid domain of the second proximity probe only when the proximity probes are bound in proximity, i.e. the hybridisation is reliant on the probes being bound to the target analyte in proximity. The strength of the interaction of the binding domain (or parts thereof) of the preformed circle oligonucleotide markers with the nucleic acid domains of the proximity probes may be achieved by manipulating the complementarity of the sequence of the binding domain (or parts thereof) to the sequences of the nucleic acid domains of the proximity probes. For instance, altering the length and/or sequence identity of the region of complementarity (the part of the nucleic acid domain that is complementary to the binding domain, or part(s) thereof, of the markers) between the binding domain (or parts thereof) and the nucleic acid domains of the proximity probes.

In a preferred embodiment the preformed circle oligonucleotides (i.e. markers) comprise a binding domain (i.e. the part of the binding domain capable of hybridising to the nucleic acid domain of said first proximity probe) with at least 95%, preferably 96, 97, 98, 99 or 100% sequence identity to the region of complementarity of the nucleic acid domain of said first proximity probe and/or comprise a binding domain (i.e. the part of the binding domain capable of hybridising to the nucleic acid domain of said second proximity probe) with less than 100%, preferably less than 95, 94, 93, 92, 91 or 90% sequence identity to the region of complementarity of the nucleic acid domain of said second proximity probe. In a particularly preferred embodiment the binding domain (i.e. the part of the binding domain capable of hybridising to the nucleic acid domain of said second proximity probe) comprises at least 70%, preferably at least 75 or 80% sequence identity to the region of complementarity of the nucleic acid domain of said second proximity probe, e.g. between 70-100%, 70-95%. 70-90%, 75-85% sequence identity.

In a further embodiment of the invention the preformed circle oligonucleotides (i.e. markers) comprise a binding domain (i.e. the part of the binding domain capable of hybridising to the nucleic acid domain of said first proximity probe) with a sequence of at least 8, preferably 9, 10, 12, 15 or 20 nucleotides that is complementary to at least a part of nucleic acid domain of said first proximity probe and/or comprise a binding domain (i.e. the part of the binding domain capable of hybridising to the nucleic acid domain of said second proximity probe) with a sequence of less than 20, preferably less than 15, 12, 10, 9, or 8 nucleotides sequence that is complementary to at least a part of the nucleic acid domain of said second proximity probe.

In yet another embodiment of the invention where the proximity probes are the markers of the invention, the nucleic acid domains of the probes are not ligated, but instead hybridise to each other to template a nucleic acid extension reaction, e.g. a nucleic acid polymerase can extend these ends by adding NTPs thus forming a detectable nucleic acid template as described above and in U.S. Pat. Nos. 7,306,904 and 6,511,809. Again, one of the probes would be provided at a constant concentration and the other probe would be provided as a composition of differently labelled proximity probes (each with a different nucleic acid domain) in a predefined ratio. Amplification of the extension products, using any appropriate means and as described below, would give rise to the different signals.

Alternatively, the markers may interact with the nucleic acid domains of a set (e.g. a pair) of proximity probes so as to form a nucleic acid molecule from which the signal is generated, e.g. a circularised nucleic acid molecule generated by a ligation reaction templated by the nucleic acid domain(s) of the proximity probes. In such an embodiment, where the nucleic acid domain of one proximity probe may act as a ligation template, an nucleic acid domain of another proximity probe may alternatively (or in addition) act as primer for amplification e.g. rolling circle amplification of the circularised nucleic acid molecule (see further below).

In a further preferred embodiment of the invention the marker of the invention may be the "gap" or "cassette" oligonucleotide of a proximity ligation assay, as described in detail below. In this embodiment, the nucleic acid domains of the proximity probes are unable to ligate without the addition of a "gap" oligonucleotide that effectively bridges the gap between the proximity probe nucleic acid domains. The gap oligonucleotide may be held in place by a splint oligonucleotide that is capable of hybridising to both probe nucleic acid domains and the gap oligonucleotide. On the addition of, e.g. a ligase enzyme, the gap oligonucleotide is joined to the proximity probe nucleic acid domains to form a "unique" nucleic acid sequence, which may be detected in accordance with the disclosures herein. The effect of extending the dynamic range of the assay is achieved by using a composition of gap (and splint) oligonucleotides with different sequences in a predefined ratio. In one embodiment, the gap oligonucleotide may be provided as nucleic acid domain of a third proximity probe. In another embodiment, the gap oligonucleotide may be pre-hybridized to the splint oligonucleotide. An example of this embodiment is depicted in FIG. 7.

Hence, the gap oligonucleotide may be viewed as a marker, wherein the binding domain and the reporter domain may consist of the same sequence and the gap oligonucleotide binds or interacts with the nucleic acid domains of the proximity probes indirectly, i.e. via the splint oligonucleotide. Alternatively viewed, the gap oligonucleotide may be viewed as a first part of the marker, comprising the reporter domain, wherein the second part of the marker is provided as the splint oligonucleotide, comprising the binding domain and a region (sequence) that is complementary to the gap oligonucleotide, which functions as the reporter domain.

In yet a further embodiment the marker may be the splint oligonucleotide, comprising the binding domain and the reporter domain, wherein the gap between the nucleic acid molecules of the proximity probes is "filled-in" using the splint oligonucleotide as a template for a polymerase reaction (see further below). The extended nucleic acid domain may be ligated to the nucleic acid domain of the other proximity probe (templated by the splint oligonucleotide), thereby incorporating a sequence that is complementary to the reporter domain of the splint, which itself is capable of acting as the reporter domain. Hence, this embodiment may alternatively be viewed as generating the gap oligonucleotide, i.e. marker, in situ.

Thus, in a further embodiment, the markers comprise an oligonucleotide binding domain and preferably an oligonucleotide reporter domain. In a preferred embodiment, marker is an oligonucleotide and the binding domain of the marker is separated into two parts, where the first part is at the 5' end of the oligonucleotide and the second part is at the 3' end of the oligonucleotide. In one embodiment, the markers are padlock probes.

In yet a further embodiment, the binding domain of the marker may be in two or more parts which are adjacent, i.e. adjacent within the sequence of the oligonucleotide. The two parts may be directly adjacent, e.g. a continuous sequence of nucleotides, or indirectly adjacent, e.g. wherein the parts are separated by an intervening sequence, i.e. a non-binding domain sequence. In one embodiment, the markers are preformed circle oligonucleotides, preferably wherein a first part of the two part binding domain is complementary to a first target sequence, e.g. a nucleic acid domain of a first proximity probe, and the second part of the two part binding domain is complementary to a second target sequence, e.g. a nucleic acid domain of a second proximity probe. Alternatively viewed, the marker may be seen as having more than one binding domain. In a preferred embodiment each binding domain, or each part of the binding domain, binds to a different target sequence. In a particularly preferred embodiment, the second binding domain, or second part of the binding domain, binds to its target sequence when the first binding domain (or first part of the binding domain) is bound to its target sequence, e.g. when the target sequences (e.g. the nucleic acid domains of the proximity probes) are in proximity to each other (e.g. the proximity probes are bound to their respective target).

In a further embodiment of the invention the interaction between the markers and the nucleic acid domain is a nucleic acid hybridisation, i.e. Watson-Crick base pairing.

Hence, in one embodiment of the invention the generation of the detectable signal comprises ligation of the oligonucleotide markers to produce a circular oligonucleotide.

In yet another embodiment, detecting the signal comprises enhancing the reporter domain of the markers, e.g. by amplification. In a preferred embodiment said amplification is rolling-circle amplification and the amplification product is detected by any means appropriate in the art. In a particularly preferred embodiment, the amplification product is detected by the incorporation of labelled primers (e.g. primers specific to the reporter domain of the oligonucleotide marker) during the amplification reaction and detection comprises determining the presence or amount of said label in the sample after or during the amplification reaction. Alternatively, the amplification product may be detected by interacting said product with labelled probes, e.g. labelled with fluorophores, that interact, e.g. hybridise, specifically with the reporter domain of the marker oligonucleotide.

Thus, it will be apparent from the above description that in one embodiment of the invention the method utilises "probes" to interact with the analyte and the markers (marker composition) of the invention are used to detect that interaction by the generation of a signal, which can be detected as defined herein. In an alternative embodiment, the "probes" may be the "markers" as defined above. Thus, in one aspect of the invention the "markers" are proximity probes, which interact with the analyte to generate a signal and further examples and embodiments of proximity probe assays are described in more detail below. Where the below embodiments define aspects that are applicable to other aspects of the invention it is intended that these features be interpreted as further defining those aspects of the invention.

For instance, in one embodiment of the method of the present invention the proximity probes may be multivalent proximity probes. Such multivalent proximity probes comprise at least two, but as many as 100, analyte binding domains conjugated to at least one, and preferably more than one, nucleic acid(s).

The binding sites on the analyte for the respective analyte-binding domains of the proximity probes in a set may be the same or different. Thus, for example in the case of a homomeric protein complex or aggregate comprising two or more identical subunits or protein constituents, the analyte-binding domains of two or more probes may be the same. Where the analyte is a single molecule or comprises different sub-units or constituents (e.g. a heteromeric complex or an aggregate of different proteins), the analyte-binding domains will be different.

Since the length of the nucleic acid domain of the proximity probes can be constructed to span varying molecular distances, binding sites on the analyte for the analyte-binding domain need not be on the same molecule. They may be on separate, but closely positioned, molecules. For example, the multiple binding domains of an organism, such as a bacteria or cell, or a virus, or of a protein complex or interaction can be targeted by the methods of the present invention.

As noted above, the analyte-binding domain may bind to the analyte directly or indirectly. In the case of indirect binding, the target analyte may first be bound by a specific binding partner (or affinity ligand), and the analyte-binding domain of the proximity probe may bind to the specific binding partner. This enables the design of proximity probes as universal reagents. For example the analyte-specific binding partner may be an antibody, and a universal proximity probe set may be used to detect different analytes by binding to the Fc regions of the various different analyte-specific antibodies.

The nucleic acid domains of the proximity probes may be regarded as the nucleic acid "tags" which interact to form a detectable product, which may be detected to report the detection of the analyte. Where the proximity probes are acting as an intermediary molecule the detectable product acts as the target analyte for the markers of the invention. Alternatively, where the proximity probes are acting as the markers of the invention the detectable products are the signal.

The nucleic acid domains may thus be regarded as reactive nucleic acid functionalities which interact to provide the signal by means of which the analyte is detected (for example to form a signal-giving product (e.g. they may be ligated together to form a ligation product) or to mediate the formation or assist in the formation of a signal-giving product, e.g as a ligation template and/or primer, for example as an RCA primer). Put another way, the nucleic acid domains may be regarded as "detection tags", which may interact to form a "detectable" tag or product. When two or more analytes are present in the same sample they may be detected simultaneously using two or more sets of proximity probes, each set of proximity probes being designed to form on interaction a unique nucleic acid sequence "detectable tag". These unique "detectable tags" may be detected and quantified (optionally after amplification) separately using methods well known in the literature including liquid chromatography, electrophoresis, mass spectrometry, DNA array technology and multi-colour real-time PCR.

As described above, proximity probe based detection assays are well described in the prior art, e.g. WO 97/00446, WO 01/61037, WO 03/044231, WO 2005/123963 and WO 2007/107743, which are hereby incorporated by reference. Other proximity assays are also known and described in the art, for example in WO 2007/044903 and WO 2009/012220, also incorporated herein by reference. Thus, it is clear that the skilled person would be capable of modifying the detection methods as described herein using methods disclosed in the art. However, particularly preferred aspects of the detections methods of the invention are explained in detail below.

In one preferred method of detection of the present invention, the nucleic acid domains of first and second proximity probes may be joined together, for example by ligation. This "joining" (or "conjugation") may be direct, i.e. the respective nucleic acid domains may be directly joined to one another, or it may be indirect, i.e. the respective nucleic acid domains may be joined indirectly e.g. by joining each to one of the two ends of a further intermediary nucleic acid molecule (e.g. a "gap" oligonucleotide, also known in the art as a "a cassette" oligonucleotide). This "conjugation" or "interaction" (typically ligation) may be mediated by one or more splint oligonucleotides. As such, the splint or gap/cassette oligonucleotide may be added to the sample in the form of an independent nucleic acid, or it may be provided as the nucleic acid domain of a third proximity probe, as explained further below. The interaction (by ligation) results in the formation of a new nucleic acid molecule or sequence, which may be detected.

As mentioned above, and discussed further below, the splint oligonucleotide may hybridise to the nucleic acid domains of the first and second proximity probes, enabling their ligation.

The nucleic acid domains of the proximity probes may be a single stranded nucleic acid molecule (e.g. an oligonucleotide), a partially double stranded and partially single stranded molecule, or a double stranded molecule that includes of a region that is double stranded and a region where the two nucleic acid strands are not complementary and therefore single stranded. As such, in certain embodiments, the nucleic acid domain is made up of a single stranded nucleic acid. In other embodiments, the nucleic acid domain may be made up of two partially complementary nucleic acid strands, where the two strands include a hybridized region and non-hybridized region.

The nucleic acid domains of the proximity probes are generally of a length sufficient to allow splint-mediated interaction with the nucleic acid domain of another proximity probe when bound to a target analyte. In one embodiment of the invention, the splint oligonucleotide comprises a set of markers of the invention. Nucleic acid domains are usually in the range of between about 8 up to about 1000 nucleotides in length, where in certain embodiments they may range from about 8 to about 500 nucleotides in length including from about 8 to about 250 nucleotides in length, e.g., from about 8 to about 160 nucleotides in length, such as from about 12 to about 150 nucleotides in length, from about 14 to about 130 nucleotides in length, from about 16 to about 110 nucleotides in length, from about 8 to about 90 nucleotides in length, from about 12 to about 80 nucleotides in length, from about 14 to about 75 nucleotides in length, from about 16 to about 70 nucleotides in length, from about 16 to about 60 nucleotides in length, and so on. In certain representative embodiments, the nucleic acid domain may range in length from about 10 to about 80 nucleotides in length, from about 12 to about 75 nucleotides in length, from about 14 to about 70 nucleotides in length, from about 34 to about 60 nucleotides in length, and any length between the stated ranges. In some embodiments, the nucleic acid domains are usually not more than about 28, 29, 30, 31, 32, 33, 34, 35, 36, 37, 38, 39, 40, 41, 42, 44, 46, 50, 55, 60, 65, or 70 nucleotides in length.

The nucleic acid domains of the markers and proximity probes may be made up of ribonucleotides and/or deoxyribonucleotides as well as synthetic nucleotide residues that are capable of participating in Watson-Crick type or analogous base pair interactions. Thus, the nucleic acid domains may be DNA or RNA or any modification thereof e.g. PNA or other derivatives containing non-nucleotide backbones.

The sequence of the nucleic acid domain of the first and second proximity probes (i.e. the "detection" nucleic acid domains) may be chosen or selected with respect to the splint, which may be provided on a third proximity probe. Thus, the sequence is not critical as long as the first and second domains may hybridise to the third domain (splint). However, the sequences should be chosen to avoid the occurrence of hybridization events other than between the nucleic acid domains of the first and second proximity probes with that of splint(s). For example, the nucleic acids of the proximity probes should not be capable of hybridising to the reporter domain of the markers. Once the sequence of the nucleic acid domains is selected or identified, the nucleic acid domains may be synthesized using any convenient method.

The two components of the proximity probe or the markers of the invention are joined together either directly through a bond or indirectly through a linking group. For example, where the (analyte-)binding domain and the reporter (functional) domains are both nucleic acids, the domains may be joined by a phosphodiester bond. Alternatively, where the different domains of the markers or proximity probes comprise different components, the domains may be coupled using any appropriate means known in the art. For example, where the markers or probes comprise nucleic acid domains and protein domains they may be coupled to using methods and linkers as described below. In a preferred embodiment of the invention, the different domains of the markers and/or probes in each marker or probe set are coupled to the using the same linker.

The "coupling" or connection as described above may be by any means known in the art, and which may be desired or convenient and may be direct or indirect e.g. via a linking group. For example, the domains may be associated with one another by covalent linkage (e.g. chemical cross-linking) or by non-covalent association e.g., via streptavidin-biotin based coupling (biotin being provided on one domain and streptavidin on the other).

The two components of the blocking reagent are joined together either directly through a bond or indirectly through a linking group. Where linking groups are employed, such groups may be chosen to provide for covalent attachment of the binding domain and reporter domain through the linking group. Linking groups of interest may vary widely depending on the nature of the component domains. The linking group, when present, is in many embodiments biologically inert. A variety of linking groups are known to those of skill in the art and find use in the subject markers. In representative embodiments, the linking group is generally at least about 50 daltons, usually at least about 100 daltons and may be as large as 1000 daltons or larger, for example up to 1000000 daltons if the linking group contains a spacer, but generally will not exceed about 500 daltons and usually will not exceed about 300 daltons. Generally, such linkers will comprise a spacer group terminated at either end with a reactive functionality capable of covalently bonding to the nucleic acid domain or protein component. Spacer groups of interest may include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject markers include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

The probes and markers employed in the subject methods may be prepared using any convenient method. In representative embodiments, the (analyte)-binding domains and the reporter (functional) domains may be coupled, either directly or through a linking group. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used in covalently bonding the components together to produce the proximity probe include: hydroxy, sulfhydryl, amino, and the like. The particular portion of the different components that are modified to provide for covalent linkage may be chosen so as not to substantially adversely interfere with that component's binding affinity for its target. In other words, the covalent linkage should not inhibit the probe or marker from binding the target analyte and should not encourage the reporter domain to bind to the target analyte. Where necessary and/or desired, certain moieties on the components may be protected using blocking groups, as is known in the art, see e.g. Green & Wuts, Protective Groups in Organic Synthesis (John Wiley & Sons) (1991). Methods for producing nucleic acid/antibody conjugates are well known to those of skill in the art. See e.g. U.S. Pat. No. 5,733,523, the disclosure of which is herein incorporated by reference.

In other embodiments, probes and the markers may be produced using in vitro protocols that yield nucleic acid-protein conjugates, i.e. molecules having nucleic acids, e.g. coding sequences, covalently bonded to a protein, i.e. where the analyte-binding domain or protein component is produced in vitro from vectors which encode the proximity probe. Examples of such in vitro protocols of interest include: RepA based protocols (see e.g., Fitzgerald, Drug Discov. Today (2000) 5:253-258 and WO 98/37186), ribosome display based protocols (see e.g., Hanes et al., Proc. Natl. Acad. Sci. USA (1997) 94:4937-42; Roberts, Curr Opin Chem Biol (1999) June; 3: 268-73; Schaffitzel et al., J Immunol Methods (1999) December 10; 231: 119-35; and WO 98/54312), etc.

The term "antibody" as used herein can mean an antibody binding fragment or derivative or mimetic thereof, where these fragments, derivatives and mimetics possess the binding affinity for the target analyte. For example, antibody fragments, such as Fv, F(ab)$_2$ and Fab may be prepared by cleavage of the intact protein, e.g. by protease or chemical cleavage. Also of interest are recombinantly or synthetically produced antibody fragments or derivatives, such as single chain antibodies or scFvs, or other antibody derivatives such as chimeric antibodies or CDR-grafted antibodies, where such recombinantly or synthetically produced antibody fragments retain the binding characteristics of the above antibodies, i.e. that they are not capable of binding specifically to the target analyte. Such antibody fragments or derivatives generally include at least the $V_H$ and $V_L$ domains of the subject antibodies, so as to retain the binding characteristics of the subject antibodies. Such antibody fragments, derivatives or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments, derivatives and mimetics thereof may be obtained from commercial sources and/or prepared using any convenient technology, where methods of producing polyclonal antibodies, monoclonal antibodies, fragments, derivatives and mimetics thereof, including recombinant derivatives thereof, are known to those of the skill in the art.

The term "hybridisation" or "hybridises" as used herein refers to the formation of a duplex between nucleotide sequences which are sufficiently complementary to form duplexes via Watson-Crick base pairing. Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule. In one embodiment the nucleic acid domains of the first and second proximity probes thus contain a region of complementarity for the splint oligonucleotide, and conversely the nucleic acid domain of the splint oligonucleotide (which may comprise a set of markers of the invention) contains regions of complementarity for each of the nucleic acid domains of the first and second proximity probes.

The regions of complementarity (i.e. hybridisation regions) may have a length in the range of 4-30 bp e.g. 6-20, 6-18, 7-15 or 8-12 bp.

As noted above, in the preferred representative embodiment described above, the interaction between the nucleic acid domains of the first and second proximity probes is a joining of the respective domains. This joining may preferably be a ligation, particularly a template-directed ligation. In such a case, it will clearly be understood that the ligation template will be provided by the splint. Such a ligation may be carried out using a ligase enzyme.

As will be described in more detail below, amplification of the interaction (e.g. ligation) product may be used as part of the detection process. Accordingly, it may in some embodiments be desirable to design the splint so as to minimise any false amplification which may take place in such a step, for example any possibility of the splint acting as a template for the polymerase used in the amplification. Thus for example the splint may be provided as an RNA oligonucleotide or a DNA/RNA hybrid; Taq polymerase typically used in amplification reactions cannot use an RNA template. Alternatively, a similar effect may be achieved using a DNA splint with two short hybridisation regions; since the hybridisation is weak, such a splint will not template DNA polymerisation at the high temperatures used in PCR.

In one embodiment, the nucleic acid domains of the first and second probes may hybridise to the splint not immediately adjacent to each other, but to leave a gap between them. To enable their conjugation (e.g. ligation) a further oligonucleotide, referred to herein as a "gap" or "cassette" oligonucleotide, may hybridise to the splint in this gap, more particularly to span this gap. Such a gap/cassette oligonucleotide may be hybridised with each of its ends directly adjacent to the end of each of the respective domains, such that each such domain end may be ligated to the gap/cassette oligonucleotide to form a single new nucleic acid product. This requires two ligation events, both of which are templated by the splint. Both the 5' and the 3' end of the gap/cassette oligonucleotide are joined (ligated) to the free end of the nucleic acid domain of the first and second probe, as appropriate. The first and second domains are thus connected, or joined, via the gap/cassette oligonucleotide. Such an arrangement may add flexibility to the nucleic acid domains of the probes. The length of the gap/cassette oligonucleotide (and hence the gap between the ends of the first and second domains when hybridised to the splint) may vary, for example between 4 to 50, e.g. 6-30, 6-25, 6-22, 8-22, 10-22, 6-20, 8-20, 10-20 nucleotides.

The gap/cassette oligonucleotide, which functions as an intermediary oligonucleotide in the ligation of the first and second nucleic acid domains, may be added after the probes have been contacted with the sample. Alternatively, it may be added at the same time or it could be pre-hybridized to the splint oligonucleotide.

The gap may also be filled by extending the nucleic acid domain of whichever of the first or second proximity probe carries a free 3' end, using a polymerase. Once the gap has been filled, the ends are joined by a ligation step.

In certain embodiments a sample may be assayed for two or more different target analytes. In such embodiments, the sample is contacted with a set of markers or probes for each target analyte, such that the number of sets contacted with the sample may be two or more, e.g., three or more, four or more etc. Such methods find particular use in multiplex and high-throughput applications.

In a situation where multiple (i.e. two or more) marker sets are used, it will of course be understood that the markers of each set should not interact with the analyte of an other marker set, and also that each marker should generate a signal that is distinguishable from any other marker that is used. Thus, in the methods, uses and compositions etc. of the invention as herein defined, each marker may be defined in part (b) as not interacting with the analyte simultaneously with another marker in the sample and/or in part (c) as generating a signal that is distinguishable from the signal in another marker in the sample.

The amount of markers or probes that is added to a sample is selected to ensure that at least one non-saturated signal is produced. In embodiments that utilise proximity assays the amount of probes that is added to a sample is selected to provide a sufficiently low concentration of proximity probe in the reaction mixture to ensure that the proximity probes will not randomly come into close proximity with one another in the absence of binding to a target analyte, at least not to any great or substantial degree. As such, it is intended that only when the proximity probes bind the analyte through the binding interaction between the analyte-binding domains of the proximity probes and the binding sites of the analyte, do the proximity probes come into close proximity to one another. In representative embodiments, the concentration of the markers and probes in the reaction mixture following combination with the sample ranges from about 1 fM to 1 μM, such as from about 1 pM to about 1 nM, including from about 1 pM to about 100 nM.

Following combination of the sample and set(s) of markers and/or probes, the reaction mixture may be incubated for a period of time sufficient for the markers or probes to bind to the target (analyte), if present, in the sample. Preferably the sample is contacted with the intermediary analyte-binding molecule before addition of the set of markers. In representative embodiments, the intermediary analyte-binding molecule and sample may be pre-incubated for a period of time ranging from 5 minutes to about 24 hours prior to the addition of the markers. Preferably said pre-incubation is from about 20 minutes to 12 hours at a temperature ranging from 4 to about 50° C., preferably at room temperature, e.g. 18-30° C. Following pre-incubation, if such a step is included, the product mixture may be incubated for a period of time ranging from about 5 minutes to about 48 hours, including from about 30 minutes to about 12 hours, at a temperature ranging from about 4 to about 50° C., including from about 20 to about 37° C. Conditions under which the reaction mixture is maintained should be optimized to promote specific binding of the markers or probe to the target analyte, while suppressing unspecific interaction. Conditions should also allow for efficient and specific hybridization between the nucleic acid domains as described above.

In certain embodiments, the effective volume of the incubation mixture is reduced, at least during the portion of the incubation step in which the markers or probes are binding to target analyte, if present in the sample. In these embodiments, the effective volume of the incubation mixture may be reduced for a number of different reasons. In certain embodiments, the effective volume of the incubation mixture is reduced in order to allow for the use of medium and low affinity analyte-binding domains and/or increase the sensitivity of the assay. For example, in certain embodiments where the effective volume of the incubation mixture is reduced, the analyte-binding domains may be medium or low affinity binders, by which is meant that the analyte-binding domains may have a binding affinity for their target analyte that is less than about $10^{-4}$ M, such as about 1 mM $K_d$. In certain embodiments, the sensitivity of the assay may be increased such that the assay can detect as few as about 100 or fewer target analytes in a 1 µl sample, including as few as about 75 or fewer target analytes in a 1 µl sample, including as few as about 50 or fewer target analytes in a 1 µl sample.

In certain embodiments, a "crowding agent" or "volume excluder" is included in the mixture during the incubation step reviewed above, e.g., to reduce the effective volume of the incubation mixture during binding of the markers or probes to their target analyte. Typically, the "crowding agent" is a water soluble macromolecular material. Suitable macromolecular materials broadly comprise biocompatible natural or synthetic polymers having an average molecular weight of from about 1500 to several million, which do not specifically interact with the other reagents in the mixture, or the product. Such polymers are known in the art as "volume-excluders", as their primary function is to occupy volume in the in vitro reaction medium and provide a highly concentrated environment for biochemical reactions, e.g., approximating in vivo conditions. The volume-excluding polymers must of course be sufficiently soluble to provide the required concentration. Suitable exemplary polymers include, but are not limited to: commercially available polyethylene glycol (PEG) polymers, e.g., having an average molecular weight greater than about 2000, FICOLL polymers such as those having an average molecular weight of about 70,000, bovine plasma albumin, glycogen, polyvinylpyrrolidone, dextran, etc. PEG polymers of higher molecular weights, especially, PEG 1450, PEG 3350, PEG 6000 (also sold as PEG 8000), and PEG 20,000, having average molecular weights of about 1450, 3000-3700, 6000-7500, and 15,000-20,000, respectively, are employed in representative embodiments. PEG 6000 and PEG 8000 are employed in representative embodiments. The concentration of the volume-excluding polymers in the incubation reaction in representative embodiments falls within a range of about 5% w/v to about 45% w/v, depending upon the type of polymer and its molecular weight. In general, it is expected that a given type of polymer of higher molecular weight need be present in lower concentration than the same type of polymer of lower molecular weight to achieve the same effect on enzyme activity.

In those embodiments where a volume excluder is employed, prior to the next step of the method, the incubation mixture may be diluted to account for the presence of the volume excluder, e.g., by at least about 2-fold or more, such as at least about 5-fold or more, including at least about 10-fold or more, depending on the amount of volume excluder that is present, the nature of the dilution fluid, etc., where in representative embodiments the dilution fluid is water or some other suitable aqueous fluid of water and one or more solutes, e.g., salts, buffering agents, etc.

Instead of, or in addition to, the use of a volume excluder, the incubation mixture may be reduced in volume during incubation by removing a portion of the water from the incubation mixture, e.g., via evaporation. In these embodiments, the volume of the fluid may be reduced by at least about 2-fold or more, such as at least about 5-fold or more, including at least about 10-fold or more, as desired. Importantly, not all of the water is removed from the incubation mixture in these embodiments. Any convenient protocol may be employed for reducing the volume of the incubation mixture by removing a select portion of the water therefrom. An instrument for controlling evaporation rate by monitoring and adjusting humidity and temperature may be employed, where in certain embodiments the volume of the incubation mixture is monitored, e.g., by continuously measuring the volume of the incubation mixture, where when appropriately evaporated, the ligation and PCR-mixes may be added, as described above. As desired, a heating block could be used to enhance the evaporation. Alternatively, the volume of the incubation mixture may be reduced by filtrating out water. In representative embodiments, a size exclusion filter is used to selectively contain molecules of sizes larger than a cut off limit while smaller molecules and water is removed by passage through the filter. The force placed on the solution to move it through the filter may be by either centrifugation or vacuum suction.

As discussed above, a preferred embodiment of the invention generation of a signal of the invention involves a ligation reaction on interaction of the markers with the target analyte (wherein the target analyte may be a nucleic acid molecule generated in a proximity assay). As is known in the art, ligases catalyze the formation of a phosphodiester bond between juxtaposed 3'-hydroxyl and 5'-phosphate termini of two immediately adjacent nucleic acids when they are annealed or hybridized to a third nucleic acid sequence to which they are complementary (i.e. a template). Any convenient ligase may be employed, where representative ligases of interest include, but are not limited to: Temperature sensitive and thermostable ligases. Temperature sensitive ligases include, but are not limited to, bacteriophage T4 DNA ligase, bacteriophage T7 ligase, and *E. coli* ligase. Thermostable ligases include, but are not limited to, Taq ligase, Tth ligase, and Pfu ligase. Thermostable ligase may be obtained from thermophilic or hyperthermophilic organisms, including but not limited to, prokaryotic, eukaryotic, or archael organisms. Certain RNA ligases may also be employed in the methods of the invention.

In this ligation step, a suitable ligase and any reagents that are necessary and/or desirable are combined with the reaction mixture and maintained under conditions sufficient for ligation of the hybridized ligation oligonucleotides to occur. Ligation reaction conditions are well known to those of skill in the art. During ligation, the reaction mixture in certain embodiments may be maintained at a temperature ranging from about 4° C. to about 50° C., such as from about 20° C. to about 37° C. for a period of time ranging from about 5 seconds to about 16 hours, such as from about 1 minute to about 1 hour. In yet other embodiments, the reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 seconds to about 16 hours, such as from about 1 minute to about 1 hour, including from about 2 minutes to about 8 hours. In a representative embodiment, the ligation reaction mixture includes 50 mM Tris pH7.5, 10 mM $MgCl_2$, 10 mM DTT, 1 mM ATP, 25 mg/ml BSA, 0.25 units/ml RNase inhibitor, and T4 DNA ligase at 0.125 units/ml. In yet another representative embodiment, 2.125 mM magnesium ion, 0.2 units/ml RNase inhibitor; and 0.125 units/ml DNA ligase are employed.

Following ligation, the ligation products, e.g. ligated nucleic acid domains of the first and second probes, circularised oligonucleotide "padlock probes" etc, are detected as an indication of the presence, or as a measure of the amount and optionally the location, of analyte in the sample. In these embodiments, the ligated product comprises a single stranded nucleic acid molecule (which may be the product of the ligation of the two proximal nucleic acid domains of the first and second probes in a proximity ligation assay, and any intermediary gap/cassette oligonucleotide, if used). Said single stranded nucleic acid molecule may terminate at each end in an analyte-binding domain, in the case of a proximity ligation assay or said molecule may be, e.g. a circularised oligonucleotide.

The next step of the method following ligation step is to determine the presence of the ligated product in the reaction mixture in order to detect the target analyte in the sample. In other words, the reaction mixture is screened etc. (i.e., assayed, assessed, evaluated, tested, etc.) for the presence of any resultant ligation products in order to detect the presence of the target analyte in the sample being assayed.

The ligated product produced by the above-described methods may, in the broadest sense, be detected using any convenient protocol. The particular detection protocol may vary depending on the sensitivity desired and the application in which the method is being practiced. In certain embodiments, the nucleic acid ligation product may be directly detected without any amplification, while in other embodiments the detection protocol may include an amplification component, in which the copy number of the ligated product nucleic acid is increased, e.g., to enhance sensitivity of the particular assay. Where detection without amplification is practicable, the nucleic acid ligation product may be detected in a number of different ways. For example, one or more of the nucleic acid domains of the proximity probes may be directly labelled, e.g., fluorescently, or otherwise spectrophotometrically, or radioisotopically labelled or with any signal-giving label, such that the ligation product is directly labelled. In these embodiments, the directly labelled ligation product may be size separated from the remainder of the reaction mixture, including unligated directly labelled ligation oligonucleotides (i.e. marker oligonucleotides or cassette oligonucleotides), in order to detect the ligated nucleic acid. Alternatively, conformationally selective probes, e.g., molecular beacons (as described in greater detail below) may be employed to detect to the presence of the ligation product, where these probes are directed to a sequence that spans the ligated nucleic acids and therefore only exists in its entirety in the ligation product.

As indicated above, in certain embodiments of the subject methods, the detection step includes an amplification step, where the copy number of ligated nucleic acids is increased, e.g., in order to enhance sensitivity of the assay. The amplification may be linear or exponential, as desired, where representative amplification protocols of interest include, but are not limited to: polymerase chain reaction (PCR); isothermal amplification, etc.

Where the detection step includes an amplification step (more specifically a step of in vitro amplification of the conjugated product), the amplified product (or amplification product) may be detected, to detect the analyte.

The polymerase chain reaction (PCR) is well known in the art, being described in U.S. Pat. Nos. 4,683,202; 4,683,195; 4,800,159; 4,965,188 and 5,512,462, the disclosures of which are herein incorporated by reference. In representative PCR amplification reactions, the reaction mixture that includes the above ligated nucleic acids or ligation product (which may also be viewed as a template nucleic acid in an amplification reaction) is combined with one or more primers that are employed in the primer extension reaction, e.g., the PCR primers (such as forward and reverse primers employed in geometric (or exponential) amplification or a single primer employed in a linear amplification). The oligonucleotide primers with which the template nucleic acid (hereinafter referred to as template DNA for convenience) is contacted will be of sufficient length to provide for hybridization to complementary template DNA under annealing conditions (described in greater detail below). The primers will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers (forward and reverse primers), depending on whether primer extension, linear or exponential amplification of the template DNA is desired.

In addition to the above components, the reaction mixture produced in the subject methods typically includes a polymerase and deoxyribonucleoside triphosphates (dNTPs). The desired polymerase activity may be provided by one or more distinct polymerase enzymes. In many embodiments, the reaction mixture includes at least a Family A polymerase, where representative Family A polymerases of interest include, but are not limited to: *Thermus aquaticus* polymerases, including the naturally occurring polymerase (Taq) and derivatives and homologues thereof, such as Klentaq (as described in Barnes et al, Proc. Natl. Acad. Sci USA (1994) 91:2216-2220); *Thermus thermophilus* polymerases, including the naturally occurring polymerase (Tth) and derivatives and homologues thereof, and the like. In certain embodiments where the amplification reaction that is carried out is a high fidelity reaction, the reaction mixture may further include a polymerase enzyme having 3'-5' exonuclease activity, e.g., as may be provided by a Family B polymerase, where Family B polymerases of interest include, but are not limited to: *Thermococcus litoralis* DNA polymerase (Vent) as described in Perler et al., Proc. Natl. Acad. Sci. USA (1992) 89:5577-5581; *Pyrococcus* species GB-D (Deep Vent); *Pyrococcus furiosus* DNA polymerase (Pfu) as described in Lundberg et al., Gene (1991) 108:1-6, *Pyrococcus woesei* (Pwo) and the like. Where the reaction mixture includes both a Family A and Family B polymerase, the Family A polymerase may be present in the reaction mixture in an amount greater than the Family B polymerase, where the difference in activity will usually be at least 10-fold, and more usually at least about 100-fold. Usually the reaction mixture will include four different types of dNTPs corresponding to the four naturally occurring bases present, i.e. dATP, dTTP, dCTP and dGTP. In the subject methods, each dNTP will typically be present in an amount ranging from about 10 to 5000 µM, usually from about 20 to 1000 µM.

The reaction mixture prepared in this detection step of the subject methods may further include an aqueous buffer medium that includes a source of monovalent ions, a source of divalent cations and a buffering agent. Any convenient source of monovalent ions, such as KCl, K-acetate, NH$_4$-acetate, K-glutamate, NH$_4$Cl, ammonium sulphate, and the like may be employed. The divalent cation may be magnesium, manganese, zinc and the like, where the cation will typically be magnesium. Any convenient source of magnesium cation may be employed, including MgCl$_2$, Mg-acetate, and the like. The amount of Mg$^{2+}$ present in the buffer may range from 0.5 to 10 mM, but will preferably range from about 3 to 6 mM, and will ideally be at about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

In preparing the reaction mixture of this step of the subject methods, the various constituent components may be combined in any convenient order. For example, the buffer may be combined with primer, polymerase and then template DNA, or all of the various constituent components may be combined at the same time to produce the reaction mixture.

The amplified products of the amplification reaction may be detected using any convenient protocol, where the particular protocol employed may detect the amplification products non-specifically or specifically, as described in greater detail below. Representative non-specific detection protocols of interest include protocols that employ signal producing systems that selectively detect double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In yet other embodiments, a signal producing system that is specific for the amplification product, as opposed to double stranded molecules in general, may be employed to detect the amplification. In these embodiments, the signal producing system may include a probe nucleic acid that specifically binds to a sequence found in the amplification product (i.e. the reporter domain of the markers of the invention), where the probe nucleic acid may be labelled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probe nucleic acids include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the specifically labelled probe nucleic acids are labelled with "energy transfer" labels. As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. As used herein, "energy transfer pair" refers to any two molecules that participate in energy transfer. Typically, one of the molecules acts as a fluorescent group, and the other acts as a fluorescence-modifying group. "Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another. As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly. As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others' electronic structure. If the fluorescence-modifying group is a quenching group, this will result in the quenching group preventing the fluorescent group from even emitting light.

The energy transfer labelled probe nucleic acid, e.g., oligonucleotide, may be structured in a variety of different ways, so long as it includes a donor, acceptor and target nucleic acid binding domains. As such, the energy transfer labelled oligonucleotides employed in these embodiments of the method are nucleic acid detectors that include a fluorophore domain where the fluorescent energy donor, i.e., donor, is positioned and an acceptor domain where the fluorescent energy acceptor, i.e., acceptor, is positioned. As mentioned above, the donor domain includes the donor fluorophore. The donor fluorophore may be positioned anywhere in the nucleic acid detector, but is typically present at the 5' terminus of the detector. The acceptor domain includes the fluorescence energy acceptor. The acceptor may be positioned anywhere in the acceptor domain, but is typically present at the 3' terminus of the nucleic acid detector or probe.

In addition to the fluorophore and acceptor domains, the energy transfer labelled probe oligonucleotides also include a target nucleic acid binding domain, which binds to a target nucleic acid sequence found in the amplification product of interest (as described above), e.g., under stringent hybridization conditions (as defined above). This target binding domain typically ranges in length from about 10 to about 60 nucleotides, usually from about 15 to about 30 nt. Depending on the nature of the oligonucleotide and the assay itself, the target binding domain may hybridize to a region of the template nucleic acid or a region of the primer extension product. For example, where the assay is a 5' nuclease assay, e.g., in which a TaqMan® type oligonucleotide probe is employed, the target binding domain hybridizes under stringent conditions to a target binding site of the template nucleic acid, which is downstream or 3' of the primer binding site. In alternative embodiments, e.g., in molecular beacon type assays, the target binding domain hybridizes to a domain of a primer extension product. The overall length of the energy transfer labelled oligonucleotides employed in these embodiments, which includes all three domains mentioned above, typically ranges from about 10 to about 60 nucleotides, usually from about 15 to about 30 nucleotides.

In certain embodiments, the energy transfer labelled oligonucleotide is structured such that energy transfer occurs between the fluorophore and acceptor of the energy transfer labelled oligonucleotide probe upon fluorophore excitation when the energy transfer labelled oligonucleotide is not hybridized to target nucleic acid.

In certain embodiments, the oligonucleotide is a single stranded molecule that does not form intramolecular structures and in which energy transfer occurs because the spacing of the donor and acceptor provides for energy transfer in the single stranded linear format. In these embodiments, energy transfer also occurs between the fluorophore and acceptor of labelled oligonucleotide probe upon fluorophore excitation when the labelled oligonucleotide probe is hybridized to a target nucleic acid. Specific examples of such labelled oligonucleotide probes include the TaqMan® type probes, as described in U.S. Pat. No. 6,248,526, the disclosure of which is herein incorporated by reference (as well as Held et al., Genome Res. (1996) 6:986-994; Holland et al., Proc. Natl. Acad. Sci. USA (1991) 88:7276-7280; and Lee et al., Nuc. Acids Res. (1993) 21:3761-3766). In many of these embodiments, the target nucleic acid binding domain is one that hybridizes to, i.e. is complementary to, a sequence of the template nucleic acid, i.e. the target nucleic acid of the target nucleic acid binding domain is a sequence present in the template nucleic acid (i.e., the pseudotarget or surrogate nucleic acid).

In other embodiments, the probe oligonucleotides are structured such that energy transfer does not occur between the fluorophore and acceptor of the energy transfer labelled oligonucleotide probe upon fluorophore excitation when the energy transfer labelled oligonucleotide probe is hybridized to a target nucleic acid. Examples of these types of probe structures include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in provisional application Ser. No. 60/138,376, the disclosure of which is herein incorporated by reference). In many of these embodiments, the target binding sequence or domain comprises a hybridization domain complementary to a sequence of the primer extension product of the amplification reaction, and not to a sequence found in the pseudotarget nucleic acid.

The next step in the subject methods is signal detection from the labelled amplification products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the target nucleic acid via detection of the pseudotarget nucleic acid and/or amplification products thereof. Depending on the particular label employed, detection of a signal may indicate the presence or absence of the target nucleic acid.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter. Fluorescence is suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time.

Where the detection protocol is a real time protocol, e.g., as employed in real time PCR reaction protocols, data may be collected in this way at frequent intervals, for example once every 3 minutes, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other. The differential of signal intensities and/or ratios will allow changes in labelled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase or decrease in fluorescence from the sample in the course of or at the end of the amplification reaction is indicative of an increase in the amount of the target analyte present in the sample, e.g., as correlated to the amount of amplification product detected in the reaction mixture, suggestive of the fact that the amplification reaction has proceeded and therefore the target analyte was in fact present in the initial sample. Quantification is also possible by monitoring the amplification reaction throughout the amplification process. Quantification may also include assaying for one or more nucleic acid controls in the reaction mixture, as described above.

In this manner, a reaction mixture may readily be screened (or assessed or assayed etc.) for the presence of target analyte(s). The methods are suitable for detection of a single target analyte as well as multiplex analyses, in which two or more different target analytes are assayed in the sample. In these latter multiplex situations, the number of different sets of probes that may be employed typically ranges from about 2 to about 20 or higher, e.g., as up to 100 or higher, 1000 or higher, etc.

The analysis of many analytes simultaneously and in a single reaction using several different markers sets (multiplexing) may be enhanced by the increased specificity and sensitivity obtained when using various blocking reagents and may be further enhanced, e.g. in the context of proximity ligation assays which utilise a splint oligonucleotide. Each marker set can be designed to produce a set of unique interaction (e.g. ligation) products in proportion to the predefined ratio of the markers in that set that can be used to determine the presence or absence, quantity and/or location of the analytes being interrogated by the marker set. The interaction product may be detected directly or after amplification using any of the well established methods for analysis of nucleic acid molecules known from the literature including liquid chromatography, electrophoresis, mass spectrometry, microscopy, real-time PCR, fluorescent probes etc. Of particular interest is the combination of the proximity ligation assays which utilise a splint oligonucleotide with a "DNA array" read-out format. Several unique interaction products from a multiplexed proximity assay may be hybridized to a standardized DNA array carrying a number of oligonucleotide sequences (tags) complementary to the ligation product sequences. Each interaction product hybridized to the array may be identified by its location on the DNA array and the detected intensity in a given hybridization spot will be indicative of the quantity of that specific interaction product and hence also of the analyte giving rise to that interaction product. Detection of the interaction products may be accomplished by spectrometry, fluorescence, radioisotopes etc. Fluorescent moieties may conveniently be introduced into the interaction products using fluorescently labelled primers or fluorescently labelled nucleotides in the amplification reaction (PCR). The DNA array may be a simple dot-blot array on a membrane containing a small number of spots or a high density array carrying hundreds of thousands of spots. The use of at least two markers in a predefined ratio for each analyte ensures that at least one of the signals for each analyte present in the sample will be non-saturated, i.e. above the lowest limit of detection but below the saturation point.

The detection step of the method of the invention may be modified in order to further reduce the background associated with non-specific nucleic acid hybridization events. Such modifications include adjustments to the method that will reduce any non-specific nucleic acid hybridization events. In some embodiments, a protein may be added to the mixture containing the sample and the proximity probes in order to reduce weak and non-specific DNA hybridization events. For example, E. coli single strand DNA binding protein has been used to increase the yield and specificity of primer extension reactions and PCR reactions. (U.S. Pat. Nos. 5,449,603 and 5,534,407.) The gene 32 protein (single strand DNA binding protein) of phage T4 apparently improves the ability to amplify larger DNA fragments (Schwartz, et al., Nucl. Acids Res. 18: 1079 (1990)) and enhances DNA polymerase fidelity (Huang, DNA Cell. Biol. 15: 589-594 (1996)). When employed, such a protein will be used to achieve a concentration in the reaction mixture that ranges from about 0.01 ng/µL to about 1 µg/µL; such as from about 0.1 ng/µL to about 100 ng/µL; including from about 1 ng/µL to about 10 ng/µL.

In other embodiments, double stranded nucleic acid may be used as the nucleic acid domain of the first and second proximity probes in order to reduce weak and non-specific DNA hybridization events.

As explained above, the method of the invention is designed such that a signal is generated only if there is an interaction between the markers of the invention and the target analyte. By way of example, in a proximity probe assay the interaction between the nucleic acid domains of the first and second probes (e.g ligation) should occur only if the proximity probes are bound to the analyte. However, as is the case with all assays of this type, this cannot always be guaranteed and there may be some background interaction, e.g. ligation of the nucleic acid domains, if the probes come into proximity randomly in solution (the possibility of this is reduced by requiring the nucleic acid domains of all the probes to hybridise to one another by means of the splint, in order for such interaction to occur). Thus, to further reduce or minimise the possibility of background due to unreacted (i.e. unbound) probes, blocking oligonucleotides may be used in addition to any other blocking reagent described above.

The blocking oligonucleotides bind (i.e. hybridise or anneal) to the free ends of the nucleic acid domains of the first and second proximity probes. Thus a blocking oligonucleotide may bind to the free 3' OH end of the nucleic acid domain of a 5' proximity probe and to the free 5' phosphate end of the nucleic acid domain of a 3' proximity probe. The binding of the blocking oligonucleotide may be out-competed in the presence of a high local concentration of the splint, such as occurs when all the probes are bound together on the analyte. In this way the blocking oligonucleotide may prevent the first and second domains from hybridising to the splint in the absence of analyte binding. Thus the free ends of the 5' and 3' probes may be prevented from interaction in the absence of binding to the analyte. When all the probes are bound to the analyte, the local concentration of the splint, especially when the splint forms the nucleic acid domain of a third proximity probe, is sufficient to out-compete the blocking oligonucleotides; the first and second domains hybridise to the splint and the blocking oligonucleotides are replaced.

The blocking oligonucleotides thus allow a competition-based strategy to be used to reduce background and thus further increase sensitivity of the assay.

The blocking oligonucleotides may range in length from about 4-100 nucleotides, e.g. 6-75 or 10-50. They may hybridise to a region at or near the free end of the nucleic acid domain of the first or second probe ("near" meaning within 1-20 or 1-10, e.g. 1-6 nucleotides of the free 3' or 5' end). The region of hybridisation may be 3-15 nucleotides long e.g. 3-12, 3-10, 3-8, 4-8, 3-6, 4-6.

The blocking oligonucleotides may conveniently be designed to have a hairpin structure such that the blocking oligonucleotide may be ligated to the end of proximity probes which have failed to hybridise to the splint.

The blocking oligonucleotides are typically used in an excess over the respective probes, e.g. an excess of 2-1000 fold, e.g. 20-500, 50-300, 100-500, or 100-300 fold e.g., 20, 200 or 300 fold.

In the case of detecting an analyte with markers or probes of low affinity and slow binding kinetics, the markers or probes may be contacted with the sample and incubated at a sufficiently high concentration to promote binding of the markers or probes to the analyte. This incubation step may be quickly diluted in a large volume of cold buffer (e.g., buffer that does not include the analyte, markers or probes), and a portion of this dilution subsequently added to a ligation reaction mixture. This ligation reaction mixture may contain the cassette oligonucleotide (if used), ATP and ligase enzyme. The low temperature, e.g., ranging from about 0° C. to about 20° C., including from about 4° C. to about 10° C., minimizes the dissociation of existing marker- or probe-analyte complexes while the vast dilution results in a decrease of the concentration of the unbound markers or probes, thereby lowering their reactivity and minimizing the background signal.

In such embodiments, the assay is performed by using a small incubation volume of from about 1 µl to about 20 µl, such as about 1 µl, or about 2 µl, or about 3 µl, or about 4 µl, or about 5 µl or about 6 µl, of sample, markers and/or proximity probes and then adding the cassette in a larger incubation volume of from about 8 µl to about 1.5 ml or more, such as from about 20 µl to about 1.3 ml, such as from about 50 µl to about 1 ml, such as from about 75 µl to about 800 µl, such as from about 100 µl to about 500 µl, such as from about 200 µl to about 300 µl. The effective concentration of the proximity probes in the final incubation volume is thus diluted, reducing the background while maintaining the signal since the binding between the probes and analyte does not have time to dissociate before the first and the second nucleic acid domains are ligated. This approach enables extremely high sensitivity as long as the ligation products can be concentrated from the larger volumes, such as over 100 µl or more, and then detecting the proximity dependent interaction. In such embodiments, the probe-probe interactions can be reduced by using single strand binding proteins.

Problems associated with complex samples may be further addressed by diluting the complex sample prior to the analysis. However, one advantage of the detection method of the present invention is that the marker composition may conveniently overcome the background signal associated with complex samples by ensuring that at least one signal above the limit of detection, but below saturation level, is generated per analyte, i.e. extending the dynamic range of the assay. Nevertheless, dilution of complex samples may, in combination with the marker composition of the present invention, have the effect of further reducing the background signal. In essence, the step of diluting the sample will greatly decrease the amount of proteins the probes may bind unspecifically to thereby lowering concentration of markers or probes required. While the analyte will also be diluted, the high sensitivity of the proximity probing, particularly with the extended dynamic range provided by the markers of the invention, will provide good detection and quantification.

The method of the present invention may be employed homogeneously (i.e. in solution) as described above, or alternatively heterogeneously, using a solid phase, for example, in which analyte becomes immobilised on a solid phase, permitting the use of washing steps. The use of solid phase assays offers advantages, particularly for the detection of difficult samples: washing steps can assist in the removal of inhibiting components, and analytes can be enriched from an undesirably large sample volume. Higher concentrations and greater amounts of proximity probes can be used, as unbound analytes and markers or probes can be removed by washing. The ability to remove unbound markers or probes, or markers or probes which have not interacted, by washing also means that the solid phase assay tolerates lower purity markers and probes by comparison with the homogeneous assay.

Immobilisation of the analyte on a solid phase may be achieved in various ways. Accordingly, several embodiments of the solid phase proximity ligation assay which utilises a splint oligonucleotide are contemplated. In one such embodiment using proximity probes, one (or more) of the first or second (or third, if used) proximity probes may be (or may be capable of being) immobilised on a solid phase (or solid support). The analyte can firstly be captured by the one (or more) immobilised (or immobilisable) probes and secondly be bound by subsequently added probe(s). The immobilised markers or probes may be immobilised, i.e. bound to the support, in any convenient way. Thus the manner or means of immobilisation and the solid support may be selected, according to choice, from any number of immobilisation means and solid supports as are widely known in the art and described in the literature. Thus, the markers or probes may be directly bound to the support, for example via the analyte-binding domain (e.g. chemically cross-linked), it may be bound indirectly by means of a linker group, or by an intermediary binding group(s) (e.g. by means of a biotin-streptavidin interaction). Thus, a marker or probe may be provided with means for immobilisation (e.g. an affinity binding partner, e.g. biotin or a hapten, capable of binding to its binding partner, i.e. a cognate binding partner, e.g. streptavidin or an antibody) provided on the support. The marker or probe may be immobilised before or after binding to the analyte. Further, such an "immobilisable" marker or probe may be contacted with the sample together with the support.

The solid support may be any of the well known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc.

The support may be made of glass, silica, latex or a polymeric material. Suitable are materials presenting a high surface area for binding of the analyte. Such supports may have an irregular surface and may be for example porous or particulate e.g. particles, fibres, webs, sinters or sieves. Particulate materials e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10, and e.g. not more than 6 µm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the analyte binding steps.

In another embodiment, an immobilised (or immobilisable) analyte-specific probe comprising only a binding domain (i.e. an analyte capture probe) can be used in addition to the non-immobilised markers or probes of the homogeneous assay. Thus in such an embodiment the analyte is first captured by the immobilised or immobilisable capture probe which serves only to immobilise the analyte on the solid phase, and subsequently the immobilised analyte is incubated with the markers and/or probes. In such an embodiment, the capture probe may be any binding partner capable of binding the analyte, directly or indirectly (e.g. as discussed above in relation to the analyte-binding domain of the markers and probes). More particularly, such a capture probe binds specifically to the analyte. Since this embodiment of the method requires the simultaneous binding of at least two probes (binding domains) to the analyte or analyte complex, potentially at least two different epitopes can be interrogated, conferring high specificity on the assay.

In a further embodiment, the analyte itself may be immobilised (or immobilisable) on the solid phase e.g. by non-specific absorption. In a particular such embodiment, the analyte may be present within cells, being optionally fixed and/or permeabilised, which are (capable of being) attached to a solid support.

Some of the above-described methods result in detection of proximity dependent interactions that are present in the reaction mixture, which in turn provides a measure of the amount of target analyte in the sample being assayed. The measure may be qualitative or quantitative.

Accordingly, the above described methods of detecting the presence of one or more target analytes in a complex sample finds use in a variety of different applications.

The subject methods may be used to screen a sample for the presence or absence of one or more target analytes in a sample. As indicated above, the invention provides methods of detecting the presence or quantifying the amount of one or more target analytes in a sample.

The subject methods can be employed to detect the presence of one or more target analytes in a variety of different types of samples, including complex samples having large amounts of non-target entities, where the marker composition of the subject methods allows for an extended concentration range of the target analyte(s) over equivalent methods that do not utilise the marker composition of the invention. As such, the subject methods are highly sensitive methods of detecting one or more target analytes in a simple or complex sample. The sample that is assayed in the subject methods is, in many embodiments, from a physiological source, as discussed in more detail above.

In addition to detecting a wide variety of analytes, the subject methods may also be used to screen for compounds that modulate the interaction between the analyte binding domain of the markers and probes with the binding region of the analyte i.e. the binding of the analyte-binding domain to the analyte. The term modulating includes both decreasing (e.g., inhibiting) and enhancing the interaction between the two molecules. The screening method may be an in vitro or in vivo format, where both formats are readily developed by those of skill in the art.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays find use in the a variety of methods, including methods of modulating the activity of the target analyte, and conditions related to the presence and/or activity thereof.

Also provided are kits that find use in practicing the subject methods, as mentioned above. For example, in some embodiments, kits for practicing the subject methods include the marker composition, comprising a predefined ratio of markers as described above. Said kits may further comprise at least one probe, preferably comprising an analyte-binding domain coupled to a nucleic acid domain and the kit may alternatively comprise at least one set of proximity probes as described above. As indicated above, the certain protocols will employ two or more different sets of such markers and probes for simultaneous detection of two or more target analytes in a sample, e.g., in multiplex and/or high throughput formats. As such, in certain embodiments the kits will include two or more distinct sets of markers and probes. Furthermore, additional reagents that are required or desired in the protocol to be practiced with the kit components may be present, which additional reagents include, but are not limited to one or more of the following: a ligase, gap/cassette oligonucleotide, ligatable oligonucleotides, blocking oligonucleotides, solid support for immobilisation of a marker, probe, binding domain or analyte, detection means e.g. fluorescently labelled nucleotides or oligonucleotides, pairs of supplementary nucleic acids, single strand binding proteins, and PCR amplification reagents (e.g., nucleotides, buffers, cations, etc.), and the like. In certain embodiments, the kits may include elements employed in reducing the effective volume of an incubation mixture, as reviewed above, e.g., a volume excluder. The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Accordingly, in a further aspect the present invention provides a kit for use in method for detecting an analyte in a sample, said kit comprising:

(a) a set of markers, comprising at least two markers, wherein each marker:
  (i) is capable of interacting with said analyte and generating a detectable signal
  (ii) cannot interact with the analyte simultaneously with another marker in the set;
  (iii) generates a signal that is distinguishable from the signal of another marker in the set; and
  (iv) is present in an amount capable of detecting said analyte at a range of concentrations that differs from the range of analyte concentrations detectable by other markers.

(b) optionally, at least one probe comprising an analyte-binding domain coupled to a binding-domain of a set of the markers of (a), preferably wherein the binding-domain is a nucleic acid domain;

(c) optionally at least one set of at least first and second proximity probes, comprising an analyte-binding domain and a reporter (functional) domain and wherein each probe in each probe set can simultaneously bind to the analyte, preferably wherein the reporter domain is a nucleic acid domain;

(d) optionally, means for mediating the interaction between the nucleic acids of said first and second proximity probes (e.g. a splint oligonucleotide and/or a ligase enzyme); and (e) optionally, means for detecting said signal.

A preferred aspect of the invention provides a kit for use in a method for detecting an analyte in a sample, said kit comprising:

(a) at least a pair of proximity probes each comprising a proteinaceous target-binding domain coupled to a nucleic acid domain (in particular such that said nucleic acid domains may be allowed to interact directly or indirectly when the proximity probes have bound in proximity to their respective target), said target being either the analyte or a binding partner for the analyte;

(b) a set of markers, comprising at least two markers which function to extend the dynamic range of detection of the method, wherein said set comprises at least two markers, wherein each marker is a nucleic acid molecule comprising a binding domain and a reporter domain, which gives rise to a detectable signal, and each marker:
  (i) is capable of interacting either with said nucleic acid domains (in particular when said probes have bound in proximity to their respective target) to form a nucleic acid molecule from which a detectable signal is generated, or with a nucleic acid molecule generated by interaction of said domains;
  (ii) cannot interact with said nucleic acid domains simultaneously with another marker in the set;
  (iii) generates a signal that is distinguishable from the signal of another marker in the set; and
  (iv) is present in an amount capable of detecting the analyte at a range of concentrations that differs from the range of concentrations detectable by other markers;

(c) optionally, means for mediating the interaction between the nucleic acid domains of said at least pair of proximity probes (e.g. a splint oligonucleotide and/or a ligase enzyme); and (d) optionally, means for detecting said signal.

As indicated above, the means for mediating the interaction between the nucleic acids may include one or more splint oligonucleotides and/or a ligase enzyme, and such means may optionally further comprise other reagents necessary for the ligase reaction. The means for detecting the signal, may be any of the means discussed above in the context of the assay methods, e.g. amplification means and means for detecting amplification products thereof e.g. reagents for a PCR reaction (e.g. amplification primers, and optionally polymerase and/or nucleotides, etc.) and for detecting PCR amplicons etc (e.g. Taqman® probes etc.).

The kit may further optionally comprise a gap/cassette oligonucleotide and/or blocking oligonucleotides for the first and second probes.

The kit may further optionally comprise an immobilised capture probe for the analyte, or a capture probe provided with means for immobilisation. Alternatively, the kit may comprise a solid phase for capture of, or binding to, the analyte, or one or more said markers or probes may be immobilised or provided with means for immobilisation.

BRIEF DESCRIPTION OF THE DRAWINGS

The invention will be further described with reference to the following non-limiting Examples with reference to the following drawings in which.

EXAMPLES

Example 1

General Principle

Figure 5:
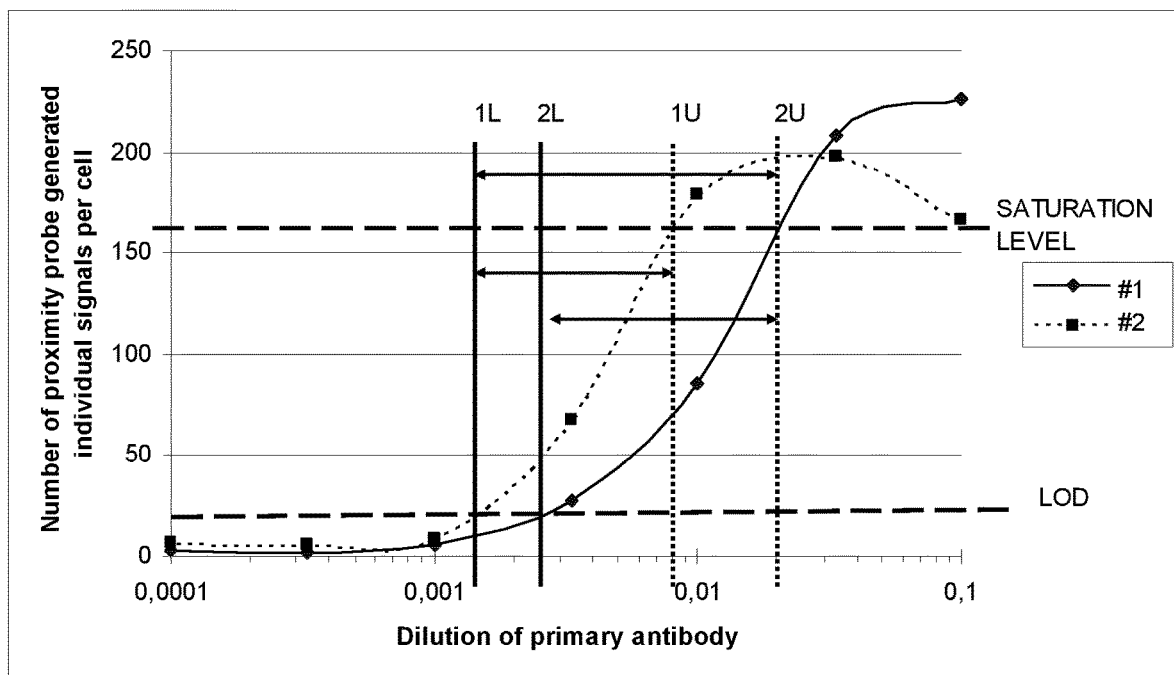
FIG. 5 shows the signal levels obtained in one experiment using two different labels for the same analyte, #2 and #1 in ratios of 1:5 of #1 over #2. The quantitative range using only label #2 is marked at line "2L" were the signal reaches above the Limit Of Detection (LOD) and stops at line "2U" were the signal reaches Saturation Levels. The Upper limit is experimentally verified by image analysis. For label #1 the respective points is marked "1L" and "1U". By combining the two labels a quantitative range from "1L" to "2U" is obtained. The signal is obtained from a dilution series of a primary antibody, representing different levels of the antigen to detect at the various dilution levels.
Figure 6:
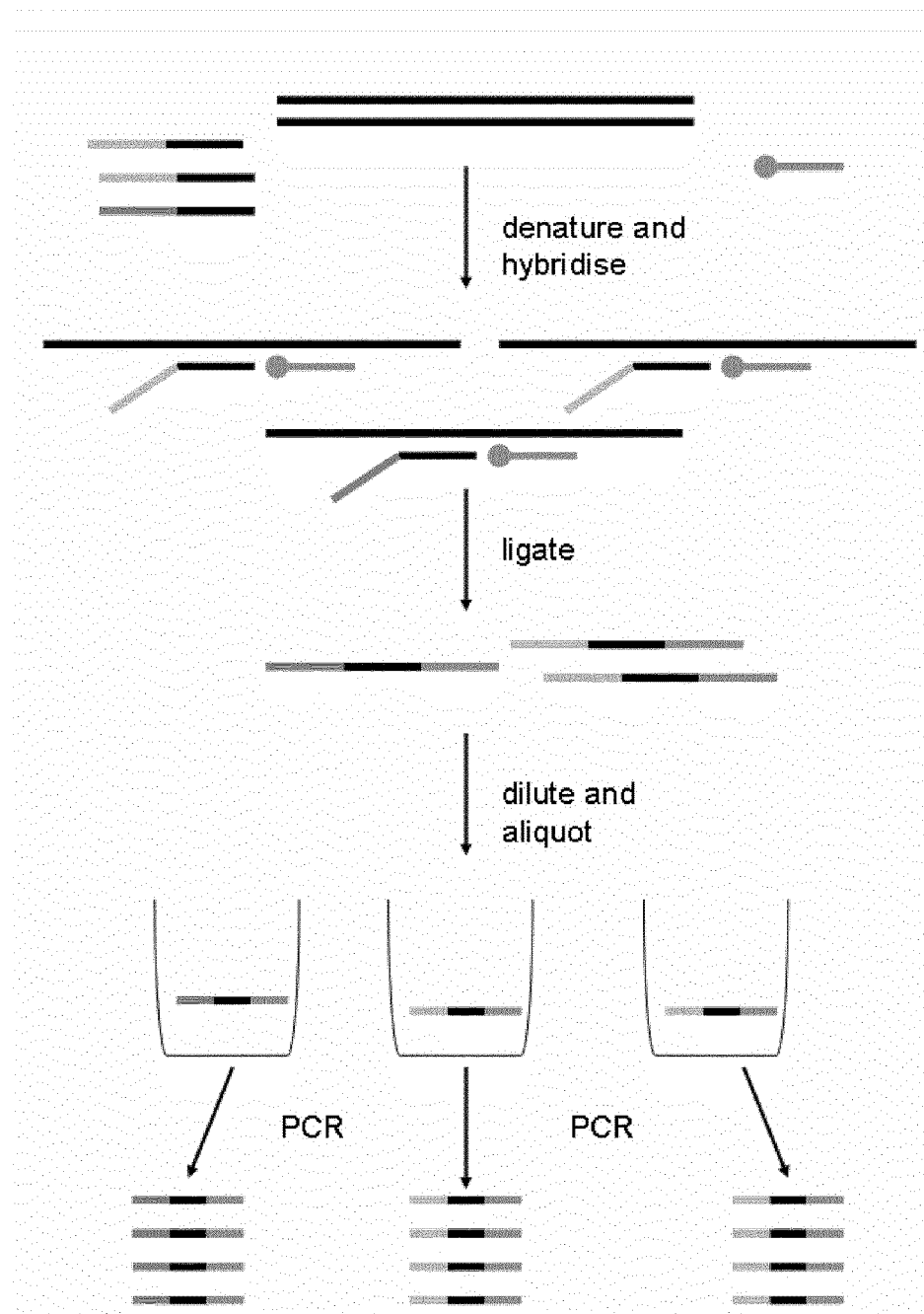
FIG. 6 shows schematic representation of a Oligonucleotide Ligation Assay (OLA), wherein two differently labelled capture probes (the labels are depicted by light gray and dark gray lines) are used to generate a substrate for digital PCR.
Figure 7:
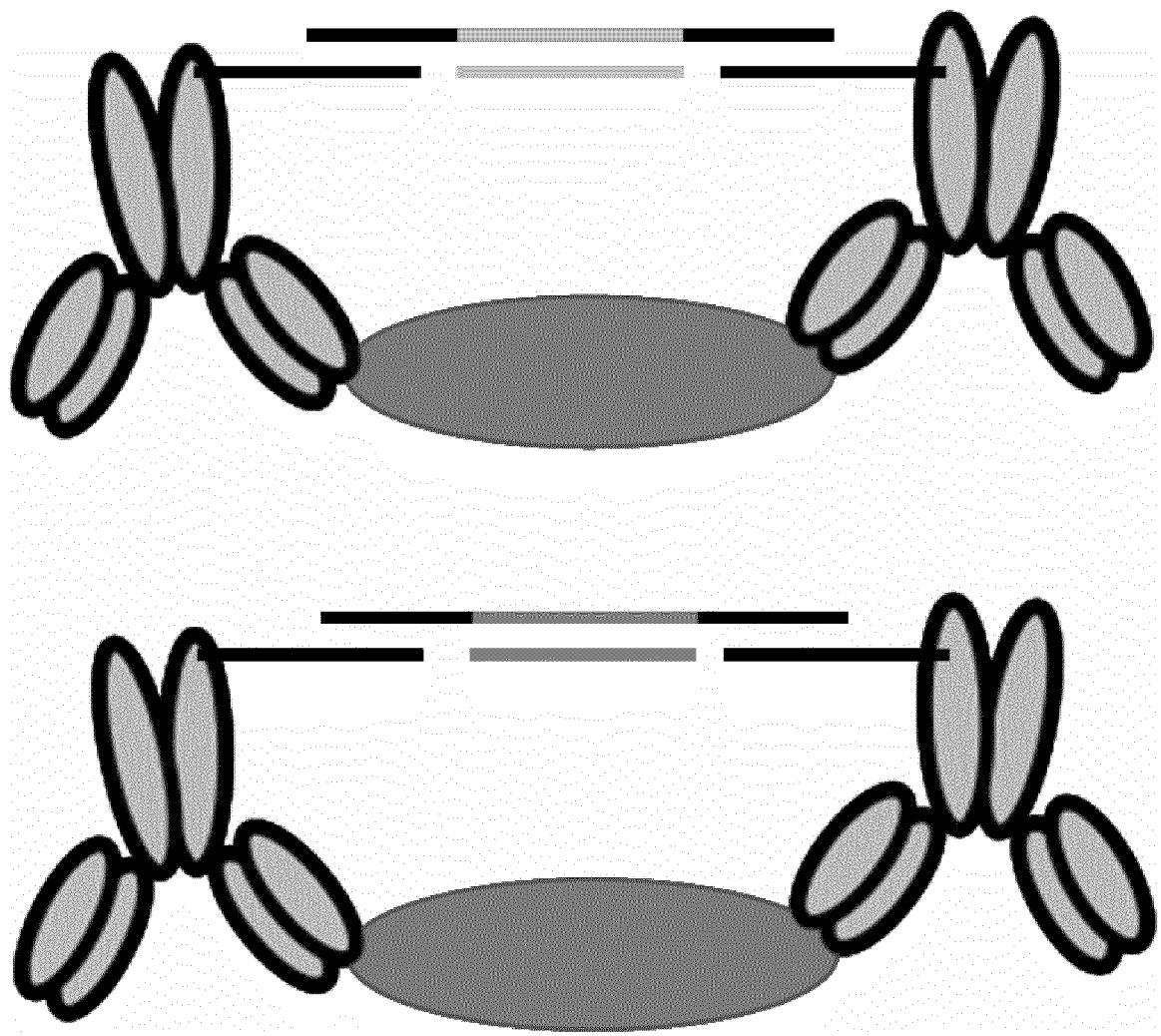
FIG. 7 shows a schematic representation of a Proximity Ligation Assay (PLA), wherein a "gap" or "cassette" oligonucleotide is used as the marker of the invention. The different gap oligonucleotides are depicted by light gray and dark gray lines.

In this specific example (see FIG. 5) the invention teaches to use different reporting nucleic acids used for circularisation (markers) but that a set of different reporting nucleic acids should circularise on the same target pair of proximity probes. The reporting nucleic acids have in this example been mixed so that 80% reports using one fluorescent label and 20% reports using another label. The labels could easily be distinguishable in a fluorescence microscope using the correct settings/filters. Any other ratio can of course be used and more than two labels could be used, e.g. three labels in the ratio of 1:5:25 and thus increasing the dynamic range even further. The exact conversion rate between the different labels is easily calculated at a point were two different labels both generating sub-saturating signals. Alternatively a standard curve/reference reaction could be used.

Detection of the HER2 Protein in Human Adenocarcinoma Cell Line

Figure 1:
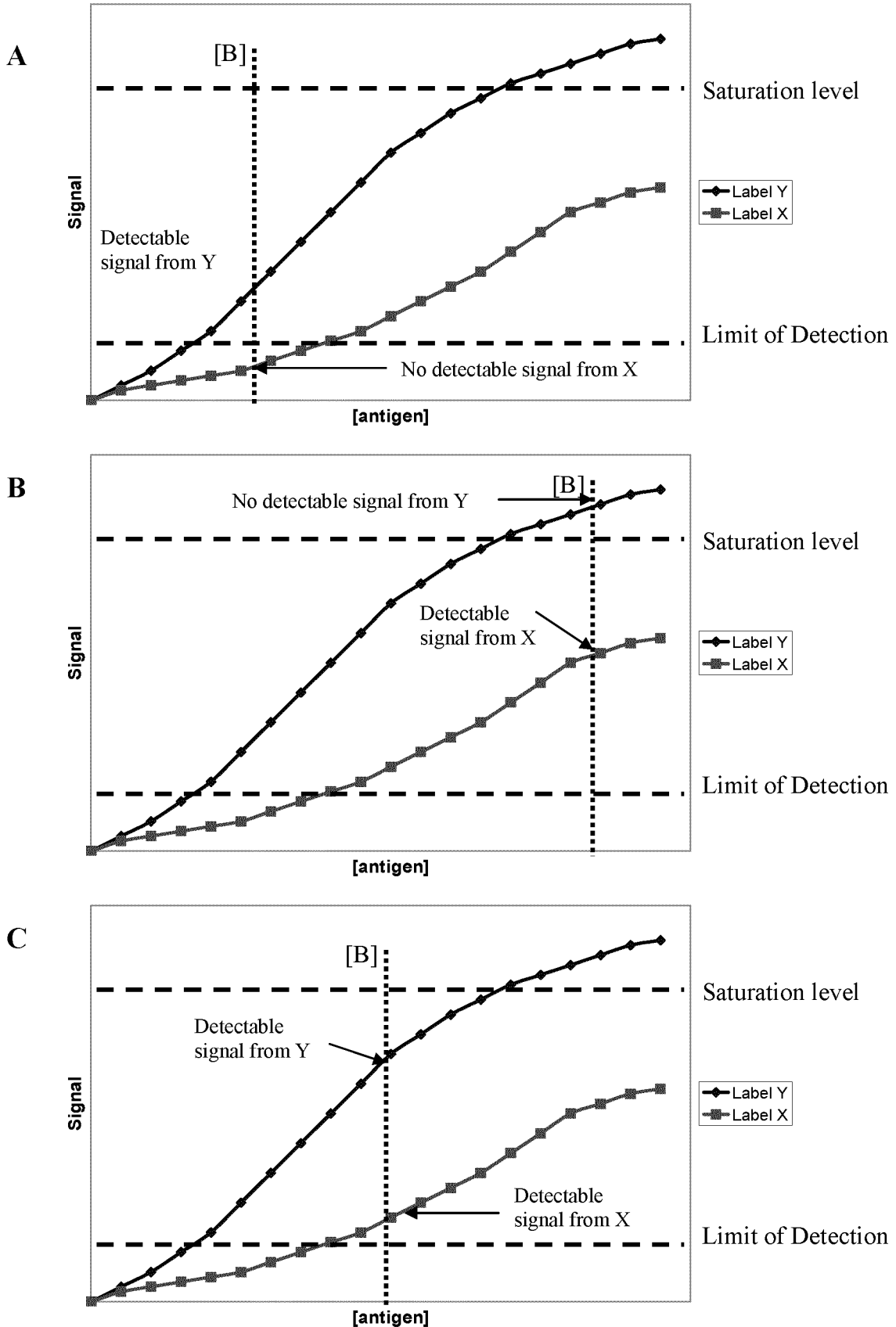
FIG. 1 shows the predicted signal generated in an assay using a marker composition of the invention wherein (A) the analyte is present at a low concentration, (B) the analyte is present at a high concentration and (C) the analyte is present at an intermediate concentration.
Figure 2:
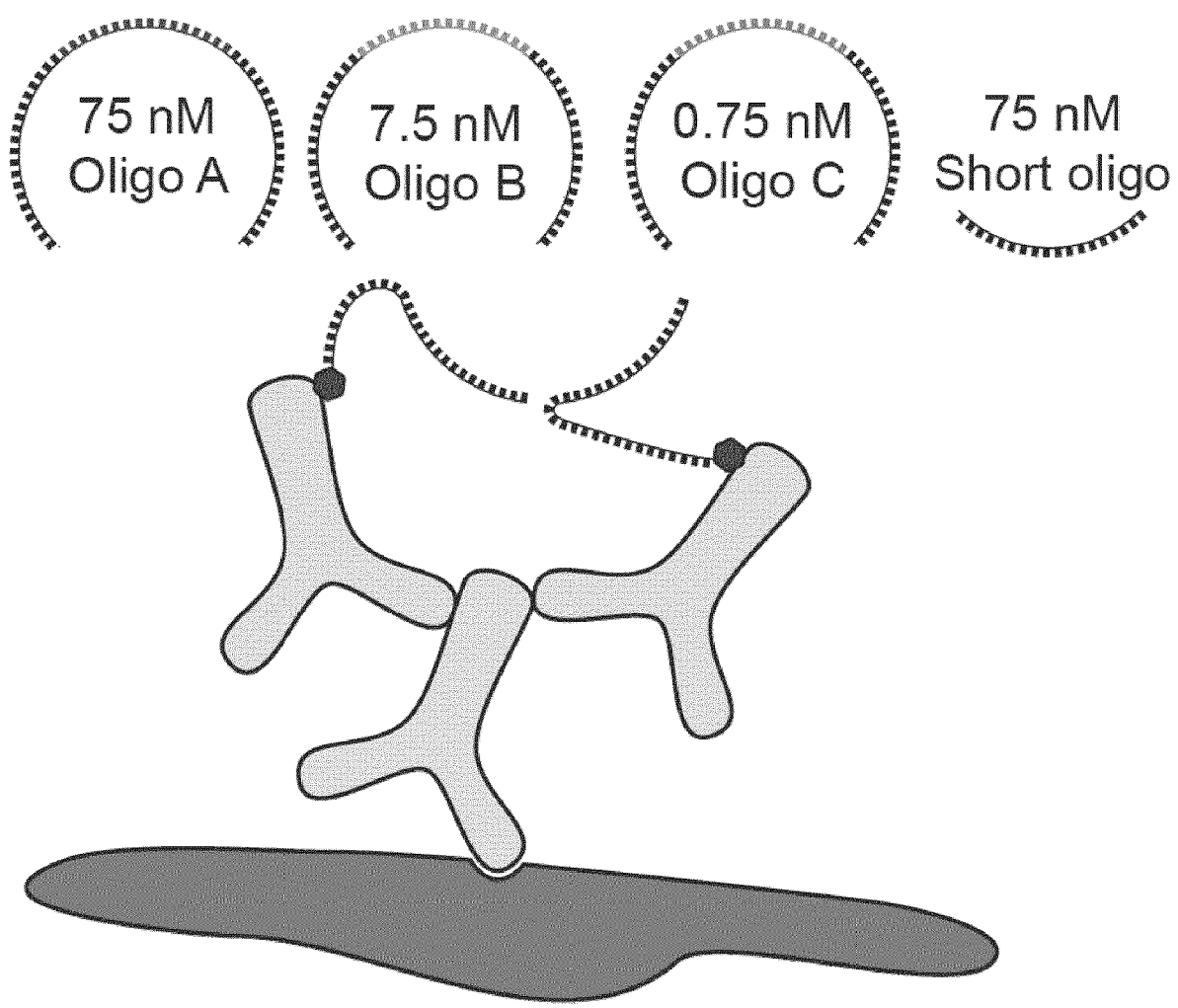
FIG. 2 shows a schematic representation of a Proximity Ligation Assay (PLA) wherein the interaction is detected using a marker composition of padlock probes in a ratio of 1:10:100, i.e. 0.75 nM:7.5 nM:75 nM.

The efficacy of the methods of the invention were demonstrated through the detection of the HER2 protein in a human adenocarcinoma cell line, SKBR3. As SKBR3 cells can have $2\times10^6$ copies per cell of the HER2 protein, this cell line is an ideal model on which to test the methods of the invention. Cell samples were treated with different concentrations of anti-HER2 antibody to simulate different HER2 expression levels. The HER protein was detected using a proximity ligation assay as depicted in FIG. 2.

Thus, in accordance with the above described invention, three padlock probes were used as the "markers", wherein each padlock probe was present at a different concentration, i.e. 75 nM, 7.5 nM or 0.75 nM. In this example each padlock probe was comprised of two oligonucleotides. The first oligonucleotide is common for all of the padlock probes and acts as a "splint" to stabilise the interaction between the nucleic acid domains of the proximity probes. The second oligonucleotide is different for each padlock probe, i.e. each second oligonucleotide comprises common sequences that can bind to the nucleic acid domains of the proximity probes and a unique nucleotide sequence such that each padlock probe is distinguishable.

Figure 3:
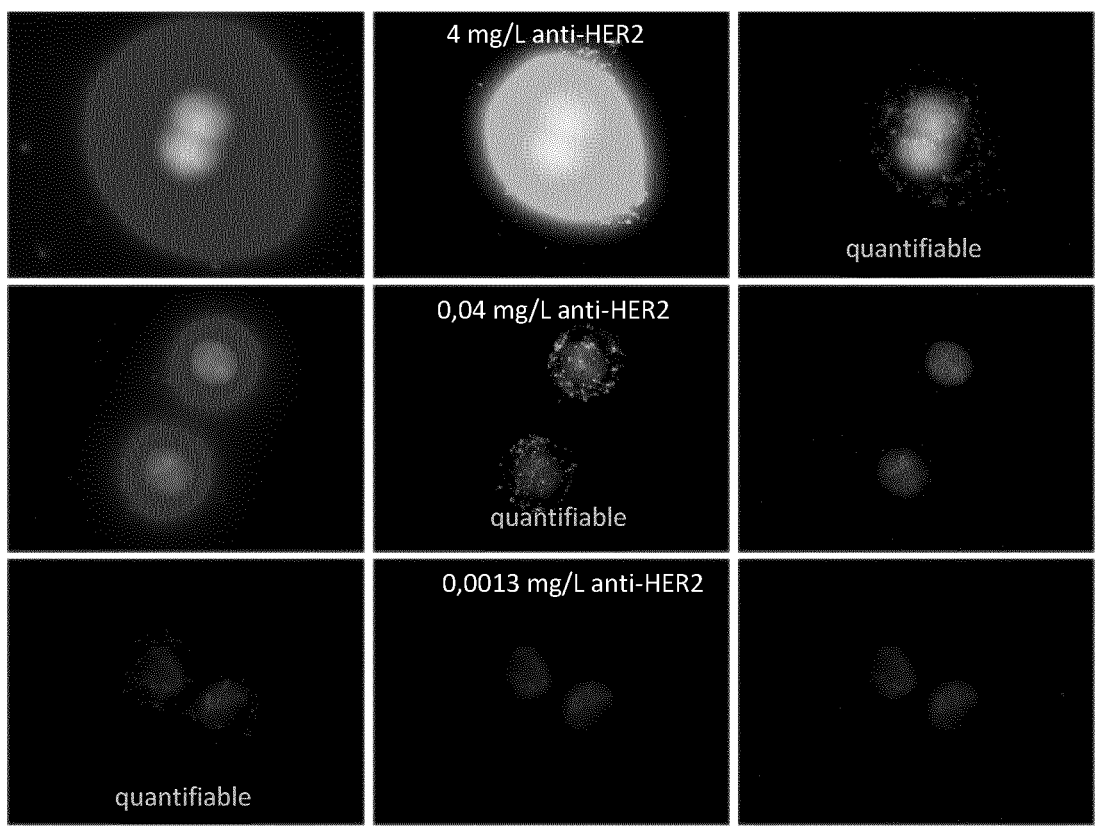
FIG. 3 shows the signal generated using the PLA-RCA depicted in FIG. 2 in an assay for the HER2 protein, wherein a non-saturated signal is detected and quantifiable at three different concentrations (Top row: 4.0 mg/L; Middle row: 0.04 mg/L; Bottom row: 0.0013 mg/L).
Figure 4:
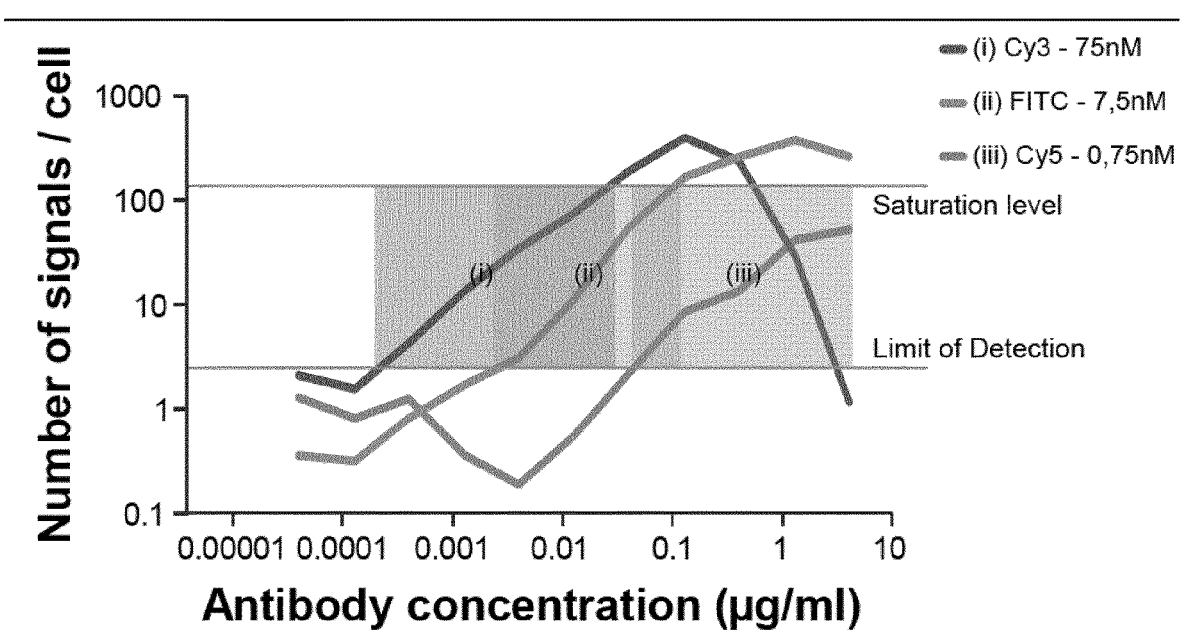
FIG. 4 shows the number of signals per area unit after detection of HER2 in FIG. 3. The coloured (shaded) squares indicate the useful range of each label.

On binding of the two oligonucleotides of the padlock probes to the nucleic acid domains of the proximity probes, the padlock probes were ligated to form circular oligonucleotides. These circular oligonucleotides were subjected to rolling circle amplification (RCA) and detection oligonucleotides were added to the sample. Each detection oligonucleotide comprises a sequence which is identical to the "distinguishable" sequence present in one of the padlock probes (i.e. the bold and underlined sequences in A-C of Table 1 match the sequences of oligonucleotides E-G, respectively) and is labelled with a different fluorescent marker. Hence, the detection oligonucleotides hybridised to the RCA products and were detected by fluorescence microscopy. The results are shown in FIGS. 3 and 4 and demonstrate that when the analyte (HER2) was present at high concentrations (4 mg/L of anti-HER2, top row of FIG. 3) the marker present at the lowest concentration (0.75 nM) yielded a quantifiable signal. Conversely, when the analyte was present at low concentrations (0.0013 mg/L of anti-HER2, bottom row of FIG. 3) the marker present at the highest concentration (75 nM) yielded a quantifiable signal. At an intermediate analyte concentration (0.04 mg/L of anti-HER2, middle row of FIG. 3) the marker at the intermediate concentration (7.5 mM) yielded a quantifiable signal.

Methods

The human adenocarcinoma cell line SKBR3 was grown at 37° C. and 5% $CO_2$ in RPMI 1640 (Sigma-Aldrich, St. Louis, Mo., USA), supplied with 10% FBS, 50 units/ml penicillin, 50 g/ml streptomycin and 2 mM L-glutamine (Sigma-Aldrich). After trypsinisation and during cell seeding, the Lab-Tek II Chamber Slide system was used, (Cat. No. 154461, Nalge Nunc International, Rochester, N.Y., USA). To one chamber on each slide, approximately 10 000 cells were added in 2 ml of growth medium before incubating them over night at 37° C. and in 5% $CO_2$. After removing the media, the cells were washed in ice-cold PBS and subsequently fixated with 3% ice-cold PFA for 10 min. After an additional washing step with ice-cold BPS, they were dehydrated in 70% EtOH and centrifuged in a Galaxy mini (VWR International, West Chester, Pa., USA) for 10 sec prior to storing them in −20° C. until use.

Each cell slide was thawed and washed in advance of marking hydrophobic borders surrounding the wells with an ImmEdge™ Pen (Vector Laboratories, Burlingame, USA). Cells were thereafter blocked at 37° C. for 90 min with blocking solution consisting of 1 mg/ml BSA (New England Biolabs Inc., Ipswich, United Kingdom), 2 µg/ml sonicated salmon sperm DNA (Invitrogen Corporation, Carlsbad, Calif., USA) and 2 mM cysteine (Sigma-Aldrich) in TBS. All incubations at 37° C. were carried out in a moisture chamber. Next, the cells were washed and incubated with primary antibody together with 0.5 mg/ml BSA, 1.65 µg/ml sterile filtered salmon sperm DNA and 1.65 mM L-cysteine in TBS. The polyclonal rabbit anti-human c-erbB-2 oncoprotein antibody (Cat. No. A0485, Dako, Glostrup, Denmark) was added in a different concentration for each of the 12 SKBR3 slides (4, 1.3, 0.4, 0.13, 0.04, 0.013, 0.004, 0.0013, 0.0004, 0.00013, 0.00004 and 0 mg/L) at 4° C. over night. After a washing step, cells were incubated with secondary antibody. During this step, each slide was incubated 4° C. over night with anti-rabbit PLUS and anti-rabbit minus (Olink Bioscience, Uppsala, Sweden) in a solution of 0.5 mg/ml BSA, 1.65 µg/ml sterile filtered salmon sperm DNA and 1.65 mM cysteine in TBS. Both secondary antibodies were diluted 10×. Next, the secondary antibody arms were hybridised with the four circularisation oligonucleotides, i.e. three 2-part padlock probes comprising a single common oligonucleotide, the so-called "splint" (A, B, C and D, see Table 1) and the padlock probes were ligated in a solution of 10 mM TrisAc, pH 7.5, 10 mM MgAc, 50 mM KAc, 1 mM ATP (Fermentas Inc., Glen Burnie, Md., USA), 200 M NaCl, 0.4 mg/ml BSA, 0.05% Tween 20, and 0.02 U/µl T4 DNA ligase (Fermentas Inc.). Final oligonucleotide concentrations were A: 75 nM, B: 7.5 nM, C, 0.75 nM and D: 75 nM. This reaction was performed at 37° C. for 40 min, before washing. Rolling circle amplification then took place in a solution consisting of 0.24 U/µl φ29 DNA polymerase (Fermentas Inc.), 1×φ29 DNA polymerase buffer (Fermentas Inc.) and 0.6 mg/ml BSA (New England Biolabs Inc.) at 37° C. for 90 min. The detection step awaited after washing and a solution of 5.16 ng/µl poly-adenine (Sigma-Aldrich), 0.17 mg/ml BSA, 1.4× saline sodium citrate buffer, 1 µM Hoechst 33342 (Sigma-Aldrich), 170 nM of each detection oligonucleotide E, F and G (targeted against rolling circle products originating from oligonucleotides A, B and C respectively) was produced in TBS. The slides were incubated for 30 min at 37° C. Subsequently, they were washed and centrifuged in a Galaxy mini (VWR International) for 10 sec and then mounted with VectaShield (Vector Laboratories, Burlingame, USA) under a Menzel-Gläser #1 cover slip (Gerhard Menzel, Glasbearbeitungswerk GmbH & Co. KG, Braunschweig, Germany).

TABLE 1

List of oligonucleotides

| Oligo | SEQ ID NO | Description | Vendor | Sequence |
| --- | --- | --- | --- | --- |
| A | 1 | Backpiece tag 1 | Integrated DNA Technology, Coralville, Iowa, USA | 5'-phosphate-CTATTAGCGTCCAGTGAATGCGAGTCCG-TCTAACTAGTGCTGGATGATCGTCCAAGAGTGTCTA-3' |
| B | 2 | Backpiece tag 2 | Integrated DNA Technology | 5'-phosphate-CTATTAGCGTCCAGTGAATGCGAGTCCG-TCTAAAGCGATCTGCGAGACCGTATAAGAGTGTCTA-3' |
| C | 3 | Backpiece tag 3 | Integrated DNA Technology | 5'-phosphate-CTATTAGCGTCCAGTGAATGCGAGTCCG-TCTAAGTATCTGCTTATGTCGCCCGAAGAGTGTCTA-3' |
| D | 4 | Splint | Eurogentec, Oslo, Norway | 5'-phosphate-GTTCTGTCATATTTAAGCGTCTTAA-3' |
| E | 5 | Detection oligo tag 1 (Cy3) | Biomers, Ulm, Germany | 5'-Cy3-CTAGTGCTGGATGATCGTCC-3' |
| F | 6 | Detection oligo tag 2 (FITC) | Eurofins MWG Operon, Ebersberg, Germany | 5'-FITC-AGCGATCTGCGAGACCGTAT-3' |
| G | 7 | Detection oligo tag 3 (HyPer5) | Genelink, Hawthorne, New York, USA | 5'-HyPer5-GTATCTGCTTATGTCGCCCG-3' |
| H | 8 | Detection oligo tag 3 (Cy5) | Biomers | 5'-Cy5-AGCGATCTGCGAGACCGTAT-3' |
| I | 9 | Antibody oligo 1 | Olink Bioscience AB | SH*-AAAAAAAAAGACGCTAATAGTTAAGACGCTTZZZ** |
| J | 10 | Antibody oligo 2 | Olink Bioscience AB | SH*-AAAAAAAAATATGACAGAACTAGACACTCTT |

*SH represents a thiol
**Z represents 2'-O-methyl-RNA

Example 2

Principle

In situ rolling circle amplification (RCA) methods, e.g. in situ proximity ligation assays and padlock probes, have a limited dynamic range over which detected molecules may be quantified. In order to provide efficient detection, the RCA products are generally large with diameters of approximately 0.8 µm. The formation of more than a hundred such RCA products per cell causes the signals to coalesce, limiting the dynamic range for digital quantification of target molecules. Here we present an approach to increase the dynamic range of proximity probe assays, exemplified using an in situ PLA.

In situ PLA involves recognition of target molecules, e.g. proteins, using pairs of target binding molecules, e.g. antibodies, with attached oligonucleotides, referred to as PLA probes. As described below, pairs of such PLA probes that are brought in proximity act as a template for hybridization and ligation of two subsequently added circularization oligonucleotides (padlock probes and a splint (short) oligonucleotide), leading to the formation of DNA circles (FIG. 2). One of the PLA probes then primes RCA using the circular DNA strand as a template, to produce RCA products that are visualized after hybridizing fluorescently labelled detection oligonucleotides. In order to allow detection of both abundant and scarce target molecules in the same reaction we have now devised reagents that give rise to three variants of the reporter DNA circles for any targeted molecule added in a concentration ratio of 1:10:100 (FIG. 2). Depending on the selection of detection oligonucleotide it is therefore possible to visualize either 100, 10 or 1 out of 111 detected target molecules. By using detection oligonucleotides with different fluorescence labels, suitable detection sensitivity can be obtained for any targeted protein. If the detection reaction is saturated in one colour, then less abundant RCA products detectable with another fluorophore can be used to quantify signals. This extends the dynamic range of the assay while reducing the need for antibody titrations or varying experimental conditions between assays (FIGS. 3 and 4). A broader range of concentration ratios or more types of circularization oligonucleotides could be used to increase the dynamic range even further if required.

The ability to increase the dynamic range is of particular value for heterogeneous samples such as tissue sections, where the amount of a specific protein may vary greatly between neighbouring cells (FIG. 3) and when the local concentration of a protein interaction is high in sub-cellular structures, as in Cajal bodies. The approach is not limited to in situ PLA, but can be applied to other RCA-based methods such as immuno-RCA and padlock probes with RCA. In general, only minor modifications of the protocols would be required to greatly enhance the dynamic range in this manner.

Materials and Methods
Cell Cultures

We grew the human adenocarcinoma cell line SKBR3 at 37° C. and 5% (vol/vol) $CO_2$ in RPMI 1640 (Sigma-Aldrich), supplemented with 10% (vol/vol) fetal bovine serum, 50 units ml$^{-1}$ penicillin, 50 g ml$^{-1}$ streptomycin and 2 mM L-glutamine (Sigma-Aldrich). Approximately 10,000 cells per well were seeded in Lab-Tek II Chamber Slide (Cat. No. 154461, Nalge Nunc International) containing 2 ml of growth medium. After removal of the media, we washed the slides in ice-cold PBS and subsequently fixated the cells with % (wt/vol) ice-cold PFA for 10 min. After washing with ice-cold PBS again, we dehydrated the cells in 70% (vol/vol) EtOH and centrifuged them in a Galaxy mini (VWR International) for 10 s before storing them in −20° C. until use. We fixated the U2OS cells instead with methanol and permeabilized them with Triton-X-100 (Sigma-Aldrich).

HER2 Analysis in SKBR3 Cells

After thawing the chamber slides and washing them with TBS, we added hydrophobic borders around the cell culture areas with an ImmEdge™ Pen (Vector Laboratories). Thereafter, we blocked the slides at 37° C. for 90 min with a blocking solution consisting of 1 mg ml$^{-1}$ BSA (New England Biolabs Inc.), 2 µg ml$^{-1}$ sonicated salmon sperm DNA (Invitrogen Corporation) and 2 mM L-cysteine (Sigma-Aldrich) in TBS. All incubations at 37° C. were carried out in a moisture chamber. Next, we washed the slides with TBS 0.05 (vol/vol) Tween 20 (as in all subsequent washes) and incubated them with an antibody incubation buffer of 0.5 mg ml$^{-1}$ BSA, 1.65 µg ml$^{-1}$ sterile filtered salmon sperm DNA, 1.65 mM Lcysteine and 0.05 % (vol/vol) Tween 20 in TBS with a polyclonal rabbit antibody targeting human c-erbB-2 (Cat. No. A0485, Dako). We added this antibody in a different concentration for each of the 12 SKBR3 wells (4, 1.3, 0.4, 0.13, 0.04, 0.013, 0.004, 0.0013, 0.0004, 0.00013, 0.00004 and 0 µg ml$^{-1}$) for incubation at 4° C. over night. After a washing step, we added two PLA probes, i.e. two batches of one rabbit IgG targeting antibody conjugated to one oligonucleotide each (oligonucleotides I and J, see Table 1 for sequences) by custom conjugation (Olink Bioscience AB), diluted 10× in the antibody incubation buffer, to the slides for incubation at 4° C. over night. Next, we hybridized circularization oligonucleotides (A: 75 nM, B: 7.5 nM, C, 0.75 nM and D: 100 nM (see Table 1 for sequences)) to the PLA probes and ligated them, through templation by oligonucleotides on the secondary antibodies, in a solution of 10 mM TrisAc, pH 7.5, 10 mM MgAc, 50 mM KAc, 1 mM ATP (Fermentas Inc.), 200 mM NaCl, 0.4 mg ml$^{-1}$ BSA, 0.05% (vol/vol) Tween 20, and 0.02γ µl$^{-1}$ T4 DNA ligase (Fermentas Inc.) at 37° C. for 40 min. After washing, we then performed RCA in a solution consisting of 0.24 Uµl$^{-1}$ φ29 DNA polymerase (Fermentas Inc.), 1×φ29 DNA polymerase buffer (Fermentas Inc.) and 0.6 mg ml$^{-1}$ BSA at 37° C. for 90 min. We then detected the RCA products, after another wash, by hybridizing 170 nM of each detection oligonucleotide E, F and G (targeting rolling circle products originating from oligonucleotides A, B and C respectively (see Table 1 for sequences)) for 30 min at 37° C. in a solution of TBS containing 5.2 ng µl$^{-1}$ poly-adenine (Sigma-Aldrich), 0.17 mg ml$^{-1}$ BSA, 1.4× saline sodium citrate buffer, 1 µM Hoechst 33342 (Sigma-Aldrich). After we then washed the slides, we dried them by centrifugation in a Galaxy mini for 10 s, and then mounted them with VectaShield (Vector Laboratories) under Menzel-Gläser 1 cover slips (Gerhard Menzel, Glasbearbeitungswerk GmbH & Co. KG). To enhance signal intensity, we stripped the rolling circle products from detection oligonucleotides and rehybridized with new ones. We did this by first heating the slides at 65° C. for 2 min and then washing with agitation in 70% (vol/vol) EtOH for approximately the same amount of time, until the cover slips fell off by themselves. We then completed rehybridization by repeating the detection and mounting steps as above.

Cajal Body Analysis in U2OS Cells

We removed slides with U2OS cells from storage in −20° C. methanol and dried them at room temperature prior to adding hydrophobic borders surrounding the wells. We thereafter blocked the slides at 37° C. for 120 min with an incubation buffer consisting of 2.5 µg ml$^{-1}$ sonicated salmon sperm DNA, 2.5 mM L-cysteine, 20% (vol/vol) sterile filtered goat serum, 0.0% (vol/vol) Tween 20 and 5 mM EDTA in PBS (referred to as Cajal incubation buffer). All incubations at 37° C. were carried out in a moisture chamber. We then washed the U2OS slides briefly in PBS and incubated them in Cajal incubation buffer with primary antibodies: 0.4 µg ml$^{-1}$ rabbit antibody to WRAP53 (Cat no. A301-442A, Bethyl Laboratories, Inc.) and 1 µg ml$^{-1}$ mouse antibody to SMN (Cat no. 610647, BD Biosciences) at room temperature for 1 h. After one washing step in PBO 0.1% (vol/vol) Tween 20 at 37° C. and two washing steps at room temperature, we incubated the slides with Cajal incubation buffer supplemented with PLA-probes: a rabbit IgG targeting antibody conjugated to oligonucleotide I and a mouse IgG targeting antibody conjugated to oligonucleotide J by custom conjugation (Olink Bioscience AB). We diluted these 2.5× and preincubated them separately in the Cajal incubation buffer for 30 min at room temperature, before mixing and applying them to slides for incubation at 37° C. for 120 min (final dilution of each secondary antibody was 5×). Subsequently, we washed the cells in 10 mM Tris-HCl pH 7.5, 0.1% (vol/vol) Tween 20 at 37° C. and twice in PBS 0.15 (vol/vol) Tween 20 at room temperature. We continued by allowing the circularization oligonucleotides (A: 4.8 nM, B: 120 nM and D: 125 nM) to hybridize to the oligonucleotides attached to the secondary antibodies in a solution of 10 mM TrisAc, pH 7.5, 10 mM MgAc, 50 mM KAc, 250 mM NaCl, 0.25 mg ml$^{-1}$ BSA and 0.05% (vol/vol) Tween 20. This reaction was performed at 37° C. for 30 min, followed by three washes in PBS 0.05 (vol/vol) Tween 20 at room temperature. All subsequent washing steps were performed in the same way. We then performed ligation and RCA before we labelled the RCA products using 15 nM each of detection oligonucleotide E and H (targeting RCA products resulting from replication of DNA circles that were formed from oligonucleotides A and B, see Table 1) in 2× saline sodium citrate buffer, containing 0.25 µgµl$^{-1}$ BSA, 7.5 ng µl$^{-1}$ poly-adenine (Sigma-Aldrich), 0.25 mg ml$^{-1}$ BSA, Hoechst 33342 (Sigma-Aldrich), 0.050 (vol/vol) Tween 20 and 10 µg ml$^{-1}$ secondary FITC-labelled donkey α-rabbit F(ab')2 fragment (Jackson ImmunoResearch Laboratories inc.) as a counterstain for WRAP53. After incubation for 30 min at 37° C., we washed the slides in PBS 0.00% (vol/vol) Tween 20 and in PBS before centrifuging them dry in a Galaxy mini for 10 s and mounting them with VectaShield under Menzel-Gläser #1 cover slips.

HER2 Analysis on Breast Cancer Tissue

Anonymized formalin-fixed and paraffin-embedded breast cancer tissue microarrays were supplied by Fredrik Pontén, in accordance with the Swedish Biobank Legislation, for this experiment. We removed paraffin by serial washes in xylene and ethanol, and then performed antigen retrieval in pH 6.0 citrate buffer (Dako Denmark A/S), heated to 125° C. for 5 min, followed by 80° C. for 20 min. Next, we washed the slide in PBS with 100 mM glycine for 15 min at room temperature to reduce autofluorescence. Afterwards, we followed the same PLA protocol as that used for the SKBR3 cells, but with minor modifications. The primary antibody concentration was 13.3 µg ml$^{-1}$, and the antibody incubation buffer did not contain Tween 20.

Equipment and Settings

We quantified the number of signals from RCA products detected with different fluorophores by automated image analysis, as described below. Throughout the concentration range of primary antibodies in SKBR3 cells, we acquired a total of 192 images of 1,388×1040×14 pixels (x- and y pixel size 0.06 µm, z step 0.77 µm), covering 1 cell each. For this, we used a Zeiss Axioplan 2 imaging microscope equipped with filters optimized for each of the fluorophores and a Zeiss AxioCam MRm camera. We imaged the tissue specimens with a 40× (1.3 NA) objective and cells with a 100× oil (1.3 NA) objective. Afterwards, we modified the images to be presented in figures for demonstrational purposes while the raw images were used for signal quantification. We altered contrast and brightness to reduce autofluorescence using Axiovision v. 4.8.2.0 (Carl Zeiss MicroImaging GmbH) for all figures, but to different extents depending on sample type. To almost completely remove autofluorescence, we used ImageJ to subtract background in all images. We gave the different fluorescence channels pseudo-colours and merged them using ImageJ.

Image Analysis

Cell Cultures

In order to quantify the number of signals per cell in a fully automated manner we used digital image analysis as follows:

We detected the fluorescent signals with a method called 3DSWD2. The method consists of two parts; a detector which is a cosine filter enhancing point-like signals, and a verifier which is a sine filter validating the result from the detector. We optimized the period T for the cosine filter, the ratio of axial to lateral resolution rz and the signal threshold Ts for signal size and signal to noise ratio. The period T should be twice the size of the signal in order to achieve optimal detection. However, a high value of T will affect the resolution of closely situated signals and we therefore used a slightly smaller period. Due to the point-spread function the spread of the signal in the axial direction is usually larger than in the lateral direction. The parameter rz describes this relationship between axial and lateral direction. We tuned all the above parameters on test images containing the same concentration (1:1:1) of long circularization oligonucleotides, thus reporting in 1:1:1 of the three fluorophores. We kept parameters T and rz constant for all channels while adjusting the threshold Ts individually for each of the colour channels since the fluorophores differ in signal intensity. We then used the same parameters for analyzing image sets where the fluorophores were presented in distinct proportions (1:10:100).

Tissue

For the tissue samples we performed a single cell analysis to quantify the number of signals in each cell. We started by segmenting the nuclei from a summation projection along the z-axis of the Hoechst 33342 light filter channel to get a 2D image with enhanced cell nuclei. After the summation projection we used a level set algorithm to segment the cells and applied a flood fill algorithm to fill holes inside the cells. Some cells were clustered together and in order to separate these cells we used a distance transform together with the watershed algorithm. Before applying the watershed segmentation to the distance transform we used an h-maxima transform to reduce over-segmentation. We used a size threshold to remove parts of the segmentation that were too small to be considered a nucleus. Moreover, we wanted to have the whole cell region segmented. Since no cytoplasm stain was available we assigned regions of the image to the closest cell nucleus by applying a distance transform to the background of the segmented nuclei image followed by watershed segmentation.

We detected signals as described above using 3DSWD with constant settings for parameters T and rz for all image channels and used the cell segmentation result and the detected signals to get a signal per cell measurement. The number of signals was also normalized to the volume of each cell. To increase the dynamic range of the signal count we combined the counts from the two channels and used the most reliable count in each end of the scale. The Cy3 channel had 10× higher signal concentration than the FITC channel and therefore we multiplied the number of detected signals in the FITC channel with 10. For cells containing less than five detectable signals in the FITC channel we counted signals in the Cy3 channel instead. Cells were thereafter colour coded according to their signal concentration, and the Hoechst image was overlaid to visualize the nuclei.

Statistical Calculations

The arithmetic mean was calculated by dividing sum of signals with the number of cells, for each antibody concentration and signal type, and the standard deviations for these as the square roots of their variances. The data presented in FIG. 4 represent the arithmetic means with respective positive standard deviations displayed.

The invention claimed is:

1. A method of detecting a peptide target or protein target in a sample, said method comprising:
   (A) providing multiple proximity probes, wherein each of the multiple proximity probes comprises a proteinaceous binding domain and a nucleic acid domain, and said proteinaceous binding domain is coupled to the nucleic acid domain;
   (B) contacting said sample with said multiple proximity probes and allowing each of the multiple proximity probes to bind, via its proteinaceous binding domain, to multiple binding sites on the target, thereby producing a binding complex comprising said target and said multiple proximity probes if the target is in the sample, wherein said multiple proximity probes in the binding complex are in proximity to one another;
   (C) providing a set of at least two markers comprising a first marker and a second marker, and optionally one or more subsequent markers;
      (i) wherein each marker in the set comprises one or more nucleic acid molecules comprising a binding domain and a reporter domain,
      (ii) wherein the reporter domain of each marker in the set includes a detectable label and the detectable label of each marker in the set is structurally different and detectably different from the detectable label of each of the other markers in the set,
      (iii) wherein the nucleic acid domain of each of at least two of the multiple proximity probes in the binding complex (a) together provide a marker binding site, or (b) generate a marker binding site by interaction of the nucleic acid domain of each of the at least two of the multiple proximity probes in the binding complex directly or indirectly with one another,
      (iv) wherein each marker in the set is capable of interacting with the marker binding site such that the first marker is capable of interacting with the marker binding site to form a first interaction product comprising the detectable label of the first marker, the second marker is capable of interacting with the marker binding site to form a second interaction product comprising the detectable label of the second marker, and each of the subsequent markers in the set is capable of interacting with the marker binding site to form a subsequent interaction product comprising the detectable label if the target is in the sample,
      (v) wherein all of the markers in the set compete to interact with the marker binding site if the target is in the sample,
      (vi) wherein the amount of each marker in the set is different, and
      (vii) wherein the first marker in the set is in an amount capable of detecting the target in a first concentration range if the target is in the sample, the second marker in the set is in an amount capable of detecting the target in a second concentration range if the target is in the sample, and the first concentration range and the second concentration range are different;
   (D) after step (C), adding said set of at least two markers to the sample and allowing said markers in the set to compete with each other for interaction with the marker binding site on the binding complex, thereby forming one or more of the first interaction product, the second interaction product, and the subsequent interaction product if the target is in the sample;
   (E) if the target is in the sample, separating the one or more of the first interaction product, the second interaction product, and the subsequent interaction product from the set of at least two markers which are not contained in the one or more of the first interaction product, the second interaction product, and the subsequent interaction product; and
   (F) detecting the detectable label in the one or more of the first interaction product, the second interaction product, and the subsequent interaction product, wherein the presence of the detectable label in the one or more of the first interaction product, the second interaction product, and the subsequent interaction product indicates the presence of the target in the sample.

2. The method of claim 1, wherein (i) said markers in the set are present in a pre-defined ratio; and/or (ii) the binding domain of each of said markers is capable of binding directly or indirectly to the marker binding site; and/or (iii) the binding domain of each marker in the set has the same or substantially the same binding affinity or specificity for the marker binding site.

3. The method of claim 2, wherein each marker in the set comprises a splint oligonucleotide and a gap oligonucleotide capable of hybridizing to the splint oligonucleotide, the interaction in step (D) comprises hybridizing the splint oligonucleotide to the marker binding site and hybridizing the gap oligonucleotide to the splint oligonucleotide such that the gap oligonucleotide is located between the nucleic acid domain of one of the proximity probes and the nucleic acid domain of another of the proximity probes on the splint oligonucleotide, and ligating the nucleic acid domain of one of the proximity probes, the gap oligonucleotide, and the nucleic acid domain of another of the proximity probes on the splint oligonucleotide together.

4. The method of claim 2, wherein the binding domain of each marker in the set is the same.

5. The method of claim 1, wherein (i) [the nucleic acid domains of the proximity probes in the bound multiple proximity probes interact by ligation to each other to generate] the marker binding site is generated by ligating the nucleic acid domain of each of the multiple proximity probes using a proximity ligation assay; or (ii) [the nucleic acid domains of the proximity probes in the bound multiple proximity probes interact by hybridisation to each other and extension of one or more of said domains to generate] the marker binding site is generated by a proximity extension assay.

6. The method of claim 1, wherein, in each marker of the set, the binding domain and the reporter domain form two parts of a single nucleic acid molecule.

7. The method of claim 6, wherein (i) the markers in the set are padlock probes, being circularisable oligonucleotides in which the binding domain of each marker in the set is separated into two parts, where the first part of the two parts is at the 5' end of each of the oligonucleotides and the second part of the two parts is at the 3' end of each of the oligonucleotides; or (ii) the markers in the set are circular oligonucleotides.

8. The method of claim 7, wherein, for each marker in the set which interacts with the marker binding site, the interaction in step (D) comprises hybridization of the two parts of each marker in the set to the marker binding site such that the two parts of each marker in the set are brought into juxtaposition on the marker binding site after the hybridization, and ligating the two parts of each marker on the marker binding site to circularize each marker in the set, wherein the one or more of the first interaction product, the second interaction product, and the subsequent interaction product comprise a circular oligonucleotide including the detectable label.

9. The method of claim 7, wherein the padlock probes hybridize to the marker binding site.

10. The method of claim 7, wherein each of the circular or circularisable oligonucleotides comprises (i) a common nucleotide sequence capable of hybridising to the marker binding site, and (ii) the detectable label, wherein the detectable label comprises a detectable nucleotide sequence.

11. The method of claim 7, wherein said markers in the set are circular oligonucleotides and the interaction in step (D) comprises binding of one or more of the markers in the set to the marker binding site, wherein the nucleic acid domain of one of the proximity probes in one or more of the first interaction product, the second interaction product, and the subsequent interaction product can serve as a primer for priming rolling circle amplification of the markers on the marker binding site.

12. The method of claim 1, wherein the markers are padlock probes, each of the padlock probes comprises two or more oligonucleotides, and the interaction in step (D) comprises hybridization of the two or more oligonucleotides to the marker binding site such that the oligonucleotides are brought into juxtaposition on the marker binding site after said hybridization to form hybridized two or more oligonucleotides and ligating the hybridized two or more oligonucleotides together, wherein the one or more of the first interaction product, the second interaction product, and the subsequent interaction product comprise a circular oligonucleotide including the detectable label.

13. The method of claim 1, wherein the detectable label of each marker in the set is a detectable nucleic acid molecule and is amplified.

14. The method of claim 13, wherein the detectable nucleic acid molecule is amplified by rolling circle amplification or polymerase chain reaction.

15. The method of claim 1, wherein the detectable label is selected from nucleic acid molecules, fluorophores, fluorescent proteins, radioactive isotopes, colorimetric detection labels, magnetic particles, particles of carbon, silver or gold, quantum dots and enzymes.

16. The method of claim 1, wherein the detectable label of each marker in the set comprises a nucleic acid and wherein said detecting the detectable label comprises amplifying the detectable label, producing an amplified detectable label, and measuring the amplified detectable label using digital PCR.

17. The method of claim 1, wherein:
in step (B), the multiple proximity probes comprise a pair of proximity probes;
in step (C), each marker in the set comprises a padlock probe comprising two oligonucleotides, wherein each of the oligonucleotides is capable of hybridizing to the marker binding site, the first oligonucleotide of the two oligonucleotides being common in each marker of the set and the second oligonucleotide of the two oligonucleotides being different in each marker of the set, and the second oligonucleotide of the two oligonucleotides comprising the binding domain separated into two parts, each of the two parts at each end of the second oligonucleotide, and the reporter domain;
step (D) comprises hybridizing said padlock probe of each marker of the set to bind to the marker binding site such that the oligonucleotides of said padlock probe are brought into juxtaposition on the marker binding site after said hybridization, and ligating the oligonucleotides of said padlock probe of each marker of the set together to circularize said padlock probe of each marker of the set, wherein the one or more of the first interaction product, the second interaction product, and the subsequent interaction product comprises a circular oligonucleotide including the detectable label; and
in step (F), the circular oligonucleotide of the one or more of the first interaction product, the second interaction product, and the subsequent interaction product is further subjected to rolling circle amplification (RCA) primed by the nucleic acid domain of one of the proximity probes in the binding complex to form a RCA product.

18. The method of claim 1, wherein the detectable label of each marker in the set is a detectable nucleic acid.

* * * * *

SEQUENCE LISTING

<160> NUMBER OF SEQ ID NOS: 10

<210> SEQ ID NO 1
<211> LENGTH: 64
<212> TYPE: DNA
<213> ORGANISM: Artificial Sequence
<220> FEATURE:
<223> OTHER INFORMATION: Oligo A

<400> SEQUENCE: 1
ctattagcgt ccagtgaatg cgagtccgtc taactagtgc tggatgatcg tccaagagtg    60
tcta                                                                 64

<210> SEQ ID NO 2
<211> LENGTH: 64
<212> TYPE: DNA
<213> ORGANISM: Artificial sequence
<220> FEATURE:
<223> OTHER INFORMATION: Oligo B

<400> SEQUENCE: 2
ctattagcgt ccagtgaatg cgagtccgtc taaagcgatc tgcgagaccg tataagagtg    60
tcta                                                                 64

<210> SEQ ID NO 3
<211> LENGTH: 64
<212> TYPE: DNA
<213> ORGANISM: Artificial sequence
<220> FEATURE:
<223> OTHER INFORMATION: Oligo C

<400> SEQUENCE: 3
ctattagcgt ccagtgaatg cgagtccgtc taagtatctg cttatgtcgc ccgaagagtg    60
tcta                                                                 64

<210> SEQ ID NO 4
<211> LENGTH: 25
<212> TYPE: DNA
<213> ORGANISM: Artificial Sequence
<220> FEATURE:
<223> OTHER INFORMATION: Oligo D

<400> SEQUENCE: 4
gttctgtcat atttaagcgt cttaa                                          25

<210> SEQ ID NO 5
<211> LENGTH: 20
<212> TYPE: DNA
<213> ORGANISM: Artificial Sequence
<220> FEATURE:
<223> OTHER INFORMATION: Oligo E
<220> FEATURE:
<221> NAME/KEY: misc_feature
<222> LOCATION: (1)..(1)
<223> OTHER INFORMATION: Labelled with Cy3

<400> SEQUENCE: 5
ctagtgctgg atgatcgtcc                                                20

<210> SEQ ID NO 6
<211> LENGTH: 20
<212> TYPE: DNA
<213> ORGANISM: Artificial sequence
<220> FEATURE:
<223> OTHER INFORMATION: Oligo F

```
<220> FEATURE:
<221> NAME/KEY: misc_feature
<222> LOCATION: (1)..(1)
<223> OTHER INFORMATION: Labelled with FITC

<400> SEQUENCE: 6
agcgatctgc gagaccgtat                                                   20

<210> SEQ ID NO 7
<211> LENGTH: 20
<212> TYPE: DNA
<213> ORGANISM: Artificial Sequence
<220> FEATURE:
<223> OTHER INFORMATION: Oligo G
<220> FEATURE:
<221> NAME/KEY: misc_feature
<222> LOCATION: (1)..(1)
<223> OTHER INFORMATION: Labelled with HyPer5

<400> SEQUENCE: 7
gtatctgctt atgtcgcccg                                                   20

<210> SEQ ID NO 8
<211> LENGTH: 20
<212> TYPE: DNA
<213> ORGANISM: Artificial sequence
<220> FEATURE:
<223> OTHER INFORMATION: Oligo H
<220> FEATURE:
<221> NAME/KEY: misc_feature
<222> LOCATION: (1)..(1)
<223> OTHER INFORMATION: Labelled with Cy5

<400> SEQUENCE: 8
agcgatctgc gagaccgtat                                                   20

<210> SEQ ID NO 9
<211> LENGTH: 35
<212> TYPE: DNA
<213> ORGANISM: Artificial sequence
<220> FEATURE:
<223> OTHER INFORMATION: Oligo I
<220> FEATURE:
<221> NAME/KEY: modified_base
<222> LOCATION: (1)..(1)
<223> OTHER INFORMATION: thiol group
<220> FEATURE:
<221> NAME/KEY: modified_base
<222> LOCATION: (33)..(35)
<223> OTHER INFORMATION: 2' O-methyl RNA
<220> FEATURE:
<221> NAME/KEY: misc_feature
<222> LOCATION: (33)..(35)
<223> OTHER INFORMATION: n is a, c, g, t or u

<400> SEQUENCE: 9
aaaaaaaaaa gacgctaata gttaagacgc ttnnn                                  35

<210> SEQ ID NO 10
<211> LENGTH: 32
<212> TYPE: DNA
<213> ORGANISM: Artificial sequence
<220> FEATURE:
<223> OTHER INFORMATION: Oligo J
<220> FEATURE:
<221> NAME/KEY: modified_base
```

-continued

```
<222> LOCATION: (1)..(1)
<223> OTHER INFORMATION: thiol group

<400> SEQUENCE: 10
aaaaaaaaaa tatgacagaa ctagacactc tt                                        32
```